US010982293B2

(12) United States Patent
Concibido et al.

(10) Patent No.: US 10,982,293 B2
(45) Date of Patent: Apr. 20, 2021

(54) METHODS FOR IMPROVING PLANT RESISTANCE TO SOYBEAN CYST NEMATODE AND COMPOSITIONS THEREOF

(71) Applicant: Monsanto Technology LLC, St. Louis, MO (US)

(72) Inventors: Vergel Concibido, Maryland Heights, MO (US); Susannah Cooper, St. Louis, MO (US); Floyd Hancock, Stuttgart, AR (US); Ivan Husic, Wildwood, MO (US); John LeDeaux, Creve Coeur, MO (US); Jennifer Yates, St. Louis, MO (US); Xianghai Ye, O'Fallon, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 15/312,540

(22) PCT Filed: May 19, 2015

(86) PCT No.: PCT/US2015/031547
§ 371 (c)(1),
(2) Date: Nov. 18, 2016

(87) PCT Pub. No.: WO2015/179378
PCT Pub. Date: Nov. 26, 2015

(65) Prior Publication Data
US 2017/0101690 A1    Apr. 13, 2017

Related U.S. Application Data

(60) Provisional application No. 62/000,604, filed on May 20, 2014.

(51) Int. Cl.
| | | |
|---|---|---|
| *C12Q 1/68* | (2018.01) | |
| *A01H 5/10* | (2018.01) | |
| *C12Q 1/6895* | (2018.01) | |
| *A01H 1/04* | (2006.01) | |
| *C12N 15/82* | (2006.01) | |
| *A01N 63/10* | (2020.01) | |

(52) U.S. Cl.
CPC ............. *C12Q 1/6895* (2013.01); *A01H 1/04* (2013.01); *A01H 5/10* (2013.01); *A01N 63/10* (2020.01); *C12N 15/8285* (2013.01); *C12Q 2600/13* (2013.01); *C12Q 2600/156* (2013.01); *Y02A 40/146* (2018.01)

(58) Field of Classification Search
None
See application file for complete search history.

(56) References Cited

U.S. PATENT DOCUMENTS

| | | |
|---|---|---|
| 7,485,770 B2 | 2/2009 | Hauge et al. |
| 2006/0225150 A1 | 10/2006 | Hauge et al. |
| 2009/0048311 A1 | 2/2009 | Williams et al. |
| 2011/0083234 A1* | 4/2011 | Nguyen ................ A01H 1/00 800/301 |
| 2012/0260368 A1 | 10/2012 | Mitchum et al. |
| 2014/0039197 A1 | 2/2014 | Miller et al. |

OTHER PUBLICATIONS

Glycine max strain Williams 82 clone GM_WBb0020M12, GenBank accession No. AC235215, published Mar. 12, 2009.*
Arús et al., "Marker-assisted selection," *Plant Breeding: Principles and prospects*, Hayward, Bosemark, Romagosa (eds.) Chapman & Hall, London, pp. 314-331 (1993).
Brim et al., "Registration of Pickett Soybeans (Reg. No. 52)," *Crop Sci.*, 6:305 (1966).
Choi et al. "A Soybean Transcript Map: Gene Distribution, Haplotype and Single-Nucleotide Polymorphism Analysis,", *Genetics*, 176:685-696 (2007).
Concibido et al., "A Decade of QTL Mapping for Cyst Nematode Resistance in Soybean," *Crop. Sci.*, 44:1121-1131 (2004).
GenBank Accession No. AC235215, Glycine max strain Williams 82 clone GM_ WBb0020M12, complete sequence [Glycine max], Mar. 12, 2009, available at: http://www.ncbi.nlm.nig.gov/nuccore/AC235215.
Golden et al., "Terminology and Identity of Infraspecific Forms of the Soybeans Cyst Nematode (*Heterodera glycines*)," Plant Disease Reporter, 54:544-546 (1970).
Grant et al., "SoyBase, the USDA-ARS soybean genetics and genomics database," *Nucleic Acids Research*, 38:D843-D846 (2010).
Guo et al., "Quantitative Trait Loci underlying Resistance to Three Soybean Cyst Nematode Populations in Soybean PI 404198A," *Crop. Sci.* 46:224-233 (2006).
Haldane, J.B.S., "The Combination of Linkage Values, and the Calculation of Distances Between the Loci of Linked Factors," *J Genet*, 8:299-309 (1919).
Hyten et al., "A High Density Integrated Genetic Linkage Map of Soybean and the Development of a 1536 Universal Soy Linkage Panel for Quantitative Trait Locus Mapping," *Crop Sci.*, 50:960-968 (2010) Herewith.

(Continued)

*Primary Examiner* — Bratislav Stankovic
(74) *Attorney, Agent, or Firm* — Arnold & Porter Kaye Scholer LLP; Lawrence Lavin, Jr.; David R. Marsh

(57) ABSTRACT

The present disclosure is in the field of plant breeding and genetics, particularly as it pertains to the genus *Glycine*. More specifically, the invention relates to methods and compositions for producing a population of soybean plants with enhanced resistance to soybean cyst nematode. The methods use the detection of molecular genetic markers linked to soybean cyst nematode resistance loci to select for plants displaying an enhanced soybean cyst nematode resistance phenotype.

21 Claims, 6 Drawing Sheets

Specification includes a Sequence Listing.

(56) References Cited

OTHER PUBLICATIONS

Hyten et al., "High-throughout SNP discovery through deep resequencing of a reduced representation library to anchor and orient scaffolds in the soybean whole genome sequence," *BMC Genomics*, 11:38 (2010).
International Search Report dated Nov. 6, 2015 in International Application No. PCT/US2015/031547.
Lander et al., "Mapping Mendelian Factors Underlying Quantitative Traits Using RFLP Linkage Maps," *Genetics* 121:185-199 (1989).
Lincoln et al., "Mapping Genes Controlling Quantitative Traits Using MAPMAKER/QTL," Whitehead Institute for Biomedical Research, Massachusetts (1990).
Meksem et al., "'Forrest' resistance to the soybean cyst nematode is bigenic: saturation mapping of the Rhg1 and Rhg4 loci," *Theoretical and Applied Genetics (TAG)*, 103(5):710-717, (2001).
Niblack et al., "Soybean Yield Losses Due to *Heterodera glycines* in Iowa," *Plant Disease*,76(9):943-948 (1992).
Niblack et al., "A Revised Classification Scheme for Genetically Diverse Populations of *Heterodera glycines*," *J Nematol.*, 34(4):279-88 (2002).
Niblack, "Soybean Cyst Nematode Management Reconsidered," *Plant Disease*, 89(10):1020-1026 (2005).
Riggs et al., "Complete Characterization of the Race Scheme for *Heterodera glycines*," *J Nematol.*, 20(3):392-395 (1988).
Schmutz J., et al., "Genome sequence of the palaeopolyploid soybean," *Nature*, 463:178-183 (2010).
Sneep et al., "Plant breeding perspectives," Wageningen (ed), Center for Agricultural Publishing and Documentation (1979).

\* cited by examiner

SEQUENCE LISTING

<160> NUMBER OF SEQ ID NOS: 76

<210> SEQ ID NO 1
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 1
aatttgagag acttttttttt ttatttttaaa gaaaagagtg atatgtaagg tctttcaatc    60
aacatgtatg attttttttt ttgctttaag aaactaatag gaaatattgg tagacctaaa   120
attcaaattt tagttacttt actcttggac cgatcctcat tttgagttta gtgactagtg   180
atgttgcagt ccaaattaag nttccagagt gttttttaaa aggtgttttt ttcgtaaata   240
catctcctat cttttttttt ccaatttata ttactttaca atttaattct caatatacat   300
t                                                                   301

<210> SEQ ID NO 2
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 2
aaaaaaatat ttcaccaatt tctcaaaaac atcttaaaaa taaaaataca aaattaaagg    60
aacatcttgt agctagaaat aaaaaatatt tcaaccaaaa aatcaaatta aaaacaaatc   120
agcatacggt tcaatgcttg agttttctct gtcgcaattt gcctgatacg gaccgtcaaa   180
aataaaaaat tgcccgatac ngacatactt ttgaatttgg tgaacttggc ttggaaaacc   240
aaaaataaaa aaatgaaatg cccacagttt caaagtggaa gacatgactt ttctggatga   300
g                                                                   301

<210> SEQ ID NO 3
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 3
aatgggccca tttggtttac aacaataatc aatttcccat gcagtggctc atgtttcaag    60
gtaaaattta tggctgagat taatttggac acacatctca atcactttca acggtttaaa   120
attaattcta tcaaagtcaa ttgtaccaaa atctaaaaca agcatgcatg gagtctatta   180
gccaataatt atatcagata nttgaagaag taattagttt ttccttgtct atactatgaa   240
gcctctatac aattaaactg attctttgac aatagaaaaa tgctaacaac acactctttc   300
a                                                                   301

<210> SEQ ID NO 4
<211> LENGTH: 301
<212> TYPE: DNA
<213> ORGANISM: Glycine max

```
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t

<400> SEQUENCE: 4 gtgacctta atgtggagga accntttcgc gagagaatct tcagcttcag ccgcgaatca    60
attcagaaac tgaaagctac tgtgaacaaa agcttgacat tgtttcctcc gccagagaac   120
ggtgacgcgg ttgagttgat ggcgaagatg agcagcgaca cgcaactgag aacggttaca   180
gagatttcgt cgtttcagtc nctgtgcgcg ctggngtggc gctgcgtgac gaaggcgcga   240
aatctcgagg ggtcgaaaan gacgacgttt cgaatggcag ttaatgttcg ccaacgcntg   300
g                                                                   301

<210> SEQ ID NO 5
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t

<400> SEQUENCE: 5
gctttgtaga tagtaaaaga aaaaaaatta tataaaataa caaatatttc taagttgttt    60
tttctttata cataaaaaag gatacattta acacaatggt ttttaaatgt gggccacgtg   120 gtttttttt catcctcctc attttacaag aaagcaaaca gtggaagaga tggtccgctt   180
cacttattcc gtgaaaacga natgtgagta taatttntcc attttatata gaaaattata   240
tatatttatc attctattaa catatcaata aaaccatccc aaaaatcaat aaaatggaaa   300
g                                                                   301

<210> SEQ ID NO 6
<211> LENGTH: 301
<212> TYPE: DNA
<213> ORGANISM: Glycine max
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 6
```

```
caatgacctc gtgcatttaa caccctaaac ttaaaaagct ggttaattta agggtagtaa    60
tagtactaat agtagtgtag tanatttaag cctctgccaa atgagttaaa agaagctgct   120
tgcaattatg aaactttacc tgagtgagtg gtaaagccgc aagaactgcc ccataaggtg   180
gctctattct gctgttttta nctttttttcc ctcgtttcag aagaaaaacg agataagcac   240
gctgctttaa tttggaagga gttacaagga accttccctt atttgctgcc cctttaagct   300
c                                                                  301
```

<210> SEQ ID NO 7
<211> LENGTH: 301
<212> TYPE: DNA
<213> ORGANISM: Glycine max
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 7

```
cctataaata tttatgaaaa anttatttaa ataatatagt ataatttagg ctatcagaaa    60
agtcatatta gttttatatg ntttgagccg aacaatgcac atgcatatca cttgaaagaa   120
atgaggganc aagtataaaa gtgattataa ggatatattatg tagctgcata tttttctttc   180
ccctctttcg gtaaaatact ngtcggtaat tgcaatccat aatctatgga ctacaggcat   240
cacatggtca gctacacatt aattttgact cctatttgac atgttatggg ttaaatgatt   300
a                                                                  301
```

<210> SEQ ID NO 8
<211> LENGTH: 301
<212> TYPE: DNA
<213> ORGANISM: Glycine max
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 8

```
ttcacttctc ctcgaatcaa taacagggag agtatcattt tcgcacttat atttagaaca    60
aatcactttg acccatagat catttngttt cgtgcatatg acccccccta accttcataa   120
gcaatgcttg attcataagg ccaaccttc ttagaccaag ttcaccatca cgtttaggaa   180
aacaaacgaa atccagttta nccagtggaa tcttttttgca tttgtagtat cccccagaca   240
aaatttcgac agtgttgatc aatttcttcg caaaatgaaa caggcaggtg aatggtctac   300
a                                                                  301
```

<210> SEQ ID NO 9
<211> LENGTH: 301

```
<212> TYPE: DNA
<213> ORGANISM: Glycine max
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t

<400> SEQUENCE: 9 ttatttttt  aatgatatat  acaaattaaa  aattaagaat  taaatgttaa  ctctttataa       60
tttgatttta  atctcaggat  ctattatttt  tcatcttaat  tcaaggntgt  tattatttat     120
ttttagtttc  ttacattatg  taagtattct  cacaagagtc  acttcctttg  tatagggata    180
ggaatggcaa  caaggtaggt  naagagcgga  tttacatatt  tcattgtta   ttccngcaaa    240 agatggttag  gatttataaa  agacaagtag  aaaaatgaaa  cttaatctca  tctccatcga    300
t                                                                        301

<210> SEQ ID NO 10
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t

<400> SEQUENCE: 10
cttagatcca  aagctatgtt  gcattgatta  acaaagtaat  cacataattt  tggtgtcatt     60
ttctaataag  aattggagtt  tcatcttgaa  agtttatgtt  gacctgtaat  gcaaacctgt    120
attgcataga  ttagtgaagt  aaaactttgt  tttttattag  agaataacat  caaaagcatt    180
tatggatctg  catgagtttt  ntcctaaaaa  ggtgtgaaat  aggggggaaa  aagccacact    240
ggatgtcaaa  accattgttc  atctggtata  tattttcatc  tccntatgat  antttttttt    300
t                                                                        301

<210> SEQ ID NO 11
<211> LENGTH: 301
<212> TYPE: DNA
<213> ORGANISM: Glycine max
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
```

```
<221> NAME/KEY: misc_feature
<222> LOCATION: (201)..(201)
<223> OTHER INFORMATION: n is a, c, g, or t

<400> SEQUENCE: 11
tgcactatca ataggaaaaa ctttnatatt ttcaatcaat tagaaatgat ggttagcatg    60
acttttgaga taattgttcc aatattagan agttctacat tactttaatg tgagtccatt   120
gataatttat aaatactatg ntctaatgta ccaaaaggtc cctaattgat aagaggttga   180
agccaataga tgtttataaa nacccatctt tcaaatccct tgagccgtct tgtagagaca   240
aaatcataac aatacattga gtaccaaaac atataatatc tctcatataa tattttgtc   300 a                                                                  301

<210> SEQ ID NO 12
<211> LENGTH: 301
<212> TYPE: DNA
<213> ORGANISM: Glycine max
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t

<400> SEQUENCE: 12
gcccagctaa aactccttgc atcatctgtg acatcaatgc tctcaacnat ttcagtatcc    60
attttatttg ntttggcgga ggcactgagc acatatgtca tatncagaca ccaaancaca   120
tacatanata tattaattna gaaggtgcga ggcaagccaa gagaaacttc ancttnccga   180
```

```
ttggatccat atgcatgtgc nggtcaatca ctcctaacat ccacagctgt cttcttttt     240 ttactgtgat attatngaga aggngcgagg caagccaaga gaagcttcac nttaaagtca    300
a                                                                   301
```

<210> SEQ ID NO 13
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 13

```
ttgtgtgtta agctatgtag taaattgtgg ttgaataagg tgccatgtta tgttggttct     60
ttattataat ttagatttgg tttagatgca aaatagaaag attcattaaa aacacaattg    120
accaaggctg aagcacaatg tgcgcttaac ctcaaccaca aaaatacaac agataatgca    180
cactgcaaca aaacttgcag naccccttgac caatactctg tgtacaaaag ccaaaatata   240
gcctataaca tacataataa gttgtgtaat tcaacaataa aaaatgacat gaaacaataa    300
t                                                                   301
```

<210> SEQ ID NO 14
<211> LENGTH: 301
<212> TYPE: DNA
<213> ORGANISM: Glycine max
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 14

```
ctcccaccac tcatcactta catcaacagt attttagca ttgtcccatc ctagaccggt      60
ttctttacca aatagtttat accaaacttg ttattctctt gaggttatca aacttgttct    120
taaactttgt tttgtgataa ctcttttctgg ttgantcctt aaatttggat gcaatttcaa   180
ttcatccatt cttggaaaaa ntagtagtga ctcgttctcc tttgaacatt ttttccaagc    240
atgctataat aaagctttca attgatttaa tgtcccaaga agttttttct ttctcaacac    300
t                                                                   301
```

<210> SEQ ID NO 15
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 15

```
ttggaaatta tgaatggggg tatgactatg ttttatgact aaaaaaagct tctataaaat     60
aattggatga atcctagaac ttagggaaat caacatatga tactttttt tttataaaga    120 ataaagacca aaaagcttc atatatattg tatcttattt ttggatcaaa aaatgaaagt    180
gtatggaact tattagtgtg nttgtcgggt gatgatgtat atgcaaatag acgagggccg   240
```
tttgatgaaa gatccacgga gtacgatgaa gtccctcgtc caatagcata tggaagagtc    300
c    301

<210> SEQ ID NO 16
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 16
gatgtcgcaa atggagggag gttgcccagt tgattacaac accataactg atctgtttct    60
tcaggttgtt tatctactgt gattaagcca ttatgaagat tagtaatata atattcctgc    120
ttcatgatca ttattgttga catatgaaat gtttctttat gtggcatcat gccatcatgc    180
ttattataca taaaaagcac ntgcccagtc tttcctctcc ttatttgtac agtaattatt    240
agtgctagac agttcatttt ttacctttt ttgtcctgtt cagagaaatc tgatccgtga    300
g    301

<210> SEQ ID NO 17
<211> LENGTH: 301
<212> TYPE: DNA
<213> ORGANISM: Glycine max
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 17 acttttctg taaagtgtat gaagttgagc acacaaaaat ttagctttta tcactataag    60
atgtcggcgt accgatacat tgnaacctca atggatcaag ttttaagtga tgacccgtgc    120
atgcatccaa gaactactgt ttgctgaatt gggttgtttt cgtgatgtgt aacgatggtg    180
ggtatacagt agaaacagtg nagcacgatg aaaatgttta tttgatagag aataatactt    240
ttctaaaatg ttttttatta ttcactaaaa cttataaaat tagaagtagg acaaagtagt    300
g    301

<210> SEQ ID NO 18
<211> LENGTH: 301
<212> TYPE: DNA
<213> ORGANISM: Glycine max
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t

<400> SEQUENCE: 18

```
aatcgattat acagttgcat ttaactgatt atagccgtgc aataatcgat tttagaagga    60
accaacaaga ttaaaaaagg catgttaaaa nagataaggg taggaggaac caatcagcca   120
gggggngatg cgatactact gcagtgttgg ttcgagctca agaatggtgt tntcatgttt   180
acagtcattc ttggaggttt ntgcgtttga aagtctgggt tgatcatgga gacataaaga   240
tggggtgaat tagtctttt gttgttaacg ttcattatct ccatggaaat aactnacatg   300
g                                                                  301
```

<210> SEQ ID NO 19
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 19

```
gatcgtagat ccctgtaagc tggcctgacc tattcccacc atcggtccgt atatgattca    60
agtttccgca tgttgctggt ttatctaagg aacaacatgt aagttggcag attaatttac   120
ttgcaggaca tacttgttca tatagctagg ttccattgct ttccaacaga aataggtac    180
aagaaaccaa cgtcaaactt ngcagataag gagggataaa taagagacg aggtgtcgcc   240
ggatttaatt ttagtagtcc acattgctca actgattaga aaattataga cgcacataat   300
t                                                                  301
```

<210> SEQ ID NO 20
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 20

```
catcgagtat cttttattt acaggccccgg cccgggcctg gacccaactt ccaccgcggc    60
tcgtttaaaa gctgcattag ccaaagcgct tgttccttat tatccattcg ccggaagggt   120
tcgctccagg cccgacggcc cgggcctcga ggtcgtttgt cgggcccagg gcgctgtctt   180
catcgaagcc tcttctgaac nttacactgc ccatgatttc caaaaggccc caagacagt   240
ggcacaatgg aggaaactat tatctctcta cgtcaccgac gttctcaaag gctctccaat   300
t                                                                  301
```

<210> SEQ ID NO 21
<211> LENGTH: 301
<212> TYPE: DNA
<213> ORGANISM: Glycine max
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 21

```
ttcttaaagt attaaatatt ttttatagca tattttttaaa taaataataa ataattttag      60
gttaagaaaa aacaattgag cgaaaaatta ttttataatn ggtctgaaaa tacttaatat     120
actgtaggaa gaattttta tagtattcct aatttttttaa atatccccct gttgattgat     180
attgcttctg tatctttcac ncgtggttat aattgattag ttgggggttc cttttggcca     240
ccaaaaaaat tactgattta tttctactat attttttcatt tatccaaaca aattgacaaa     300
a                                                                      301
```

<210> SEQ ID NO 22
<211> LENGTH: 301
<212> TYPE: DNA
<213> ORGANISM: Glycine max
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t

<400> SEQUENCE: 22

```
tttcctctct ggtcttgggc tttggccatt tttcttttat gatgtattaa taaaaaaaaa      60
tacatagatg gaattatag agcgtattgt tcaagcttaa aaatgattta tcttaaatat     120
tatgataatg gaggtataag attggtctan tagtgaaaag agaagggaat gatgcagagg     180
ttgtgtgttc aaatcttctg ntaatgaaaa aaaaaactaa caatcttttg gggtgattgc     240
gagttttttg tttttgagtt tcaaatgnaa ttttaaaat aaaatgtgtt tgacaaaaat     300
g                                                                      301
```

<210> SEQ ID NO 23
<211> LENGTH: 301
<212> TYPE: DNA
<213> ORGANISM: Glycine max
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t

<400> SEQUENCE: 23

```
tgtccctgct cttaggccaa ggaaggggga ctttatatcc tttggggaga ggcaccaaac      60
antgaggact agaatgagga cagtgccttt ccctgtgctc catgtgcctc cttttcttga     120
gagccttaat ggccttaaag ttatccaaac atggtatata atccatcgcc aatggaccct     180
tacaaggctt ccaatcaatg nttgcatcaa ccaagaaagg ttctcccttg agtgcaatc     240
tttggcgctt aggactnggc gaagaaaaan gagcgagtgg ttgcggtttg acatcgggt     300
``` a                                                                                    301

<210> SEQ ID NO 24
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t

<400> SEQUENCE: 24

```
acagcaaaag taatggtttc ttgagaaacc acaacttcta gatttattaa catttgacat      60
taggttaaaa aaaagttcct gtataaaaga tatctattct caataggtaa cagagaaacc     120
agatcaaaca aattacatat aatattaagt agctgcaaga gagatggtga gaggtatgtg     180
gggaattttg gtacaaacag naaaaaaatt tcaagtaact tctaatgcgc actcctaaaa     240
atatgattga aacaaatant cactcaagtt ttttattttt ttacttagac acccttaaaa     300
a                                                                    301
```

<210> SEQ ID NO 25
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 25

```
tgtctctagg ttttttttcac ctataattgt tcttacgagg agatataata ttagtccatt    60
ggttgagaaa aggggtgaga aaaggagag aaaaactaac atttctaata aaactaacaa     120
attaatatta atcaattata tttttttattg atgaaaaata ttatacaacc ataataaata   180
gtcaaaacta catggttgca ngactattat tagcctcttg tgggaagact ttattggggt    240
gtctatcgcc acagatgtta tcgtttagtg gtcaaggcct cccccttaata aaaagaaaag   300
t                                                                    301
```

<210> SEQ ID NO 26
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 26

```
tatgtctgaa aatggacatg gtgacaacat taaaatcagc caaacgttgt tggcgattcg     60
gtgtgtttac cttcttggct tctttcttgg tcacagcaac cttgttttct ttgtattctc    120
ccaacggtga tgctaaacaa agtcaaatgt caataccact tccccaacat cttcaccttg    180
agcagttttg ctgttttatc ngaaaccttg atggaacgca acctcgtggc cacggaattg    240
ggccaaattg ctctatcttc agccatgatt agagaaatat tgcaatggat tacgatggaa   300
c                                                                    301
```

<210> SEQ ID NO 27
<211> LENGTH: 301
<212> TYPE: DNA
<213> ORGANISM: Glycine max
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 27

```
attttctaaa atataaataa aaattactag accaagcaat atggaccttg tgctttctga      60
acatatataa cangaaaatt gcataattat ttttccacct tcaagctaaa tccgcaacgt     120
actgtggacc ctcatgagtg tgaggatctt ccacaggtca ctcacttgct ttgacatctg     180
aaagatcctt ctcgagtaaa ngtggaaac aagaacaagc ttggactggt ctacgattta     240
gtgttcttat tccaagtaat ataaaaatct taaatctcaa ggaatgatgc aatgcttcct     300
c                                                                    301
```

<210> SEQ ID NO 28
<211> LENGTH: 353
<212> TYPE: DNA
<213> ORGANISM: Glycine max
<220> FEATURE:
<221> NAME/KEY: misc_feature
<222> LOCATION: (81)..(81)
<223> OTHER INFORMATION: n is a, c, g, or t

<400> SEQUENCE: 28

```
tcttatccat atactgattg agcggttcct gaagattagc ggggaaaact tcaagagcca      60
gagacaatcg ttttccttc nccaaacagc gcctatgcaa attcttcaca atctcaagct     120
ccaattccct atcgtctcga accggaactt gctctgcttc acctaaatat accactcgag     180
cattcatcaa cttctcccat attttttcctt tctctttccc tatcgccaac ggttctccta     240
tcaccgtcgc gtcgtaaatc ctcgacgtta tcacttcctc ctcttctttc ttcttcggcg     300
gctcctccgg cgccgccgga gccggagccg attccgccgc cttctcatcc gct           353
```

<210> SEQ ID NO 29
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 29

```
tcaaagatgg atcgttgaaa caaattataa ataaagagc gacgaggttc aaaaagaaat      60
agatattgaa aaaagtaaa gtttcgagaa ataacaaaga atgagaaaaa agtaaagggt     120
ttagaaaaaa ataagaattg gaatttaaat attggttgag aatattgttc taacatgtca     180
atccataaat gttgcgtaga nttatgagcg tcgcgtgaac ttaaaaagat acgaggatga     240
tacatggttc aacatttatt acaatgatac aaattggtat ttacagacaa taattcataa     300
t                                                                    301
```

<210> SEQ ID NO 30
<211> LENGTH: 301

```
<212> TYPE: DNA
<213> ORGANISM: Glycine max
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 30
gctactaagc ttcttcctct gctggttatc caatatttgt atttcatcat atacaaatat     60
attatattgt gtaacttcgt tnatgtattg ctgattggta cttctggtac ctcttatata    120
aattgccttt ttttctgatt gaaaaaaaca aacaaacata agtgacggga actggtgttt    180
gatagatgat aacaacacct naaataaatt aaagtcatgg acaatttcgg tgactatata    240
gattcctcca accactaact atgtatttgg aaaccacttc catatcaaga tgtggaaaac    300
t                                                                    301

<210> SEQ ID NO 31
<211> LENGTH: 301
<212> TYPE: DNA
<213> ORGANISM: Glycine max
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 31
aattgagant ttttagttaa aatttgggaa tgttttccct ttatttccgc tttttatttt     60
attttcccta attaaattta gtcatcttta attatgaaat atgaatttgt aaaattattt    120
tttgcaataa tctacatatt tgttatttaa tttatgtcat gttatatttt atgttaacat    180
atctatacct tcaattttta nagattatcg tattccatac ccgaatcgtt gcagcacagg    240
cttcgacctt tctcatgcga gtccaaatgg atagatttca tgagaaaagc agcggttcag    300
t                                                                    301

<210> SEQ ID NO 32
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t

<400> SEQUENCE: 32
atttaaatat ttttttcatt taaataaatc atttttaat tattgttcct ataattttt      60 tgttggattt ttttttcttt tttcacacat cttttaatta gttcatctca tcattctata    120
tttaaaaaga ctatcacaat tgatagtgat gacatcatat tggcatcatg atgatgtcat    180
caaataccac accactaaat nctaatgtca tcaagtatta tatcagcaaa acattaaatc    240
atcgaatgat tgcacaattg agatgtcata tcatcaaatg atgatatcat caacgactan    300
```

```
a                                                                    301

<210> SEQ ID NO 33
<211> LENGTH: 794
<212> TYPE: DNA
<213> ORGANISM: Glycine max
<220> FEATURE:
<221> NAME/KEY: misc_feature
<222> LOCATION: (532)..(532)
<223> OTHER INFORMATION: n is a, c, g, or t

<400> SEQUENCE: 33
gacctgcagt cacaaaaaat atcgtcttca atagccatcc gacttttctc tcagcttctt     60
cctcaatggt tagctcatct ggaaatcaaa agagttacaa atacaagtga agtcgcgcaa    120
caaaattgca gctcaaacaa tgaaaccaaa aattgaatgg aaaaagaaaa ccactttctt    180
tgtattttac agtgcaaaat tttggcttga tgatctaatc ccaaaaatcc ccaaaatcaa    240
cattatgtac ctaccattta ctactagaag tctagaacat acaacacaag tacacatttc    300 ttcttttttaa ttatttattt ctgcacaata gattagtcct acaatttgag ggctttctcg   360
ttcttaacag aatgattcca tagcctgaca agttggtttc aaaagtaccg atagaaaaaa    420
caagatgata cctttgctat tatatgatga aaaattacga gatcgcggat tgaccccaac    480
ttttcttctg cataaatact gcaaaggggg ttaaaaaaaa cgaaacgagt tnagaataaa    540
atgaattagc aaatgggtac atacttacga cccagaaaac aaacatcaac ttcaaatatg    600
aattgaattt gaaagtgatt gcttttttcc ttctttaaat aataaagggt taaaactgaa    660
caaaggcaaa gacaaggatt acagagaaca ttacattaga gaacttagct gctagggcgc    720
gcattttgct gaagctcaca acactcccta actcttcatc aaaatctgat cagtgatgac    780
actgcaggtc gact                                                     794

<210> SEQ ID NO 34
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t

<400> SEQUENCE: 34
acctatgata tctatttaaa aacttgaaca ttatctgcaa ctgattgcta caaaaatgac     60
cattagcata actatgaaaa aaattacgaa gcataatata ctccaattta agaagcggct    120
acataatgca aaacctgtgg agagttttga cctttgccca tcatttattt gggagacagt    180
acatacatga cctgagttag nttgaatcta tcaagcatgg atacttcatc tccttattgt    240
attcgggtgt ccgtntccga cacgacatcg acattttcaa ttaatttttt caagagatga    300
g                                                                   301

<210> SEQ ID NO 35
<211> LENGTH: 301
<212> TYPE: DNA
<213> ORGANISM: Glycine max
<220> FEATURE:
<221> NAME/KEY: misc_feature
<222> LOCATION: (2)..(2)
<223> OTHER INFORMATION: n is a, c, g, or t
```

<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 35

```
tngtaaacaa aaaaaagaat cgttaaagca atattttgc gctaactctg tctcatgaat    60
ttccatcacc aatacaacac tgctaatgca actcgtcgtc atttaacgct cacgttttnt   120
gttccctgag aagtaaaaa gtgttaaaac gtagcatctc aaacactacg agatctcaaa   180
tacgcgattc tgaagctttt ntgtgatcaa tgaagttcga ccctatccca atcgattcat   240
gctccaaaga acaccaaacg atctataagg aatggttcaa ttgtgttgat ttagttatag   300
c                                                                  301
```

<210> SEQ ID NO 36
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 36

```
atgactgtga ttcactaaaa atagtatttt tagtattata agatatatta aaaaaatcta    60
acttaattga ttgaatatgt atttgagtta tgataaaaat tttataatat gattcgtata   120
gataaaaaaa tatatatata ttatatatat gataaatttt ttataattct atttcatatt   180
gtcacatctt tgcatggacc naatcattaa cgtcattttt ttccaaccta aaacaacatg   240
acatggatat gtctccgcca caggggagac tgtagtgttg cttcgtgcgc ctccatatac   300
t                                                                  301
```

<210> SEQ ID NO 37
<211> LENGTH: 301
<212> TYPE: DNA
<213> ORGANISM: Glycine max
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 37

```
aagacgcaag ttgattttct gggtaagaaa gaggtgaagg cagtgttgac gcaaagcatg    60
tttaaaattg aactgaantg aagngtgaag ctgaaaagtt ctctttgtgt gtgtgtgtgt   120
gtgttgcgtt gtagagagag agaaattgaa tgcagtaagt ttgaagaatg cgatatgata   180
tgggtatgga ttggggaagg naggaaagat aagggattga atcagatcag caatactaat   240
aggattcacc aatggcaatc cctaatctgt tctgcttttg ccatgtcacc aactgctcca   300
t                                                                  301
```

<210> SEQ ID NO 38
<211> LENGTH: 645
<212> TYPE: DNA
<213> ORGANISM: Glycine max
<220> FEATURE:
<221> NAME/KEY: misc_feature
<222> LOCATION: (564)..(564)
<223> OTHER INFORMATION: n is a, c, g, or t

<400> SEQUENCE: 38

```
agtcacggtc aatacatttg gaaaattctg ttcacatatt ttaattaaga aaataaagga      60
gtttgtttat gctgcaattt atgatctaga tccaatatag ggaagatgaa tgctagtaag     120
gcactattta ttgggtaaaa tccatgtggg tcccaatcca tatttactag ttctcactcc     180
gtacttagtg taacttacat gtgtcatccg attatggagt gttgtgctag catttctctt     240
atatagggaa ttagggatac aaaatggctt tccctacttt tcgtgggcaa ccccaatttg     300
ataacttggc cactttatgg ctagacttca gcctaattta tgtactagat atagtatatg     360
aatttataca taacttcaca tgccctgaaa ttttccactt gatttgcagg caattgtgac     420
agaagaggat ggaatggagt caatagctca tagatttctt tctgctgctg tcaaggtaga     480
gttccatcca cctgattcta tttttgatga aatgtttctg gcttgaaatt attactatat     540
ttattattgt attttaacac ttgnctttac aacatgtagt ataatactat aattcactc      600
atgcaagttt ccaggtccat ctttacaaaa ttgtaaatac taaca                    645
```

<210> SEQ ID NO 39
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 39

```
tgttttcacc ccaaaaataa ttagacctac agatattact attaaattag acatgtttat      60
tttaaatggt ccgcaaagac cgtggacaaa aacgtttagc ccgctagtta aataggtcaa     120
gctaaaaagc ccatagccca tgcgggctgt aggttaagca agttgtccat ggaccagagc     180
ccaaatgccc agctctagaa ntggcctaca aggtataatc caagtaacta gtagcttagg     240
attttttaaac atatgtcaaa gtttggttct tgtctatgca aatcgagcaa catttgtaga     300
t                                                                     301
```

<210> SEQ ID NO 40
<211> LENGTH: 301
<212> TYPE: DNA
<213> ORGANISM: Glycine max
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 40

```
atcacaacgt caaaaaaata tataaaaaaa attacattat cattataaaa aatgagttcc      60
atcataagtt atggtaaaga taatttaaat aaaaagaaaa ttagcataaa tataatatgc     120
aatttagtta gattttcaca ataaccagca aaanccaagc catactgtac aaaaataaaa     180
```

```
aacatgtgat acattctccc naatgatgga taaattggca gatcaaccta aatacggtgc    240
tagaccctga tttatgtcaa acaaatgacg tggcttagaa gaaatacact atggtcaatc    300
a                                                                    301
```

```
<210> SEQ ID NO 41
<211> LENGTH: 387
<212> TYPE: DNA
<213> ORGANISM: Glycine max
<220> FEATURE:
<221> NAME/KEY: misc_feature
<222> LOCATION: (102)..(102)
<223> OTHER INFORMATION: n is a, c, g, or t

<400> SEQUENCE: 41
```

```
cttagggacc aaattgcaga aactgaaaac tgatcaaaac cctgttgtag atgcaaaggt     60
taagaagaca tcgaagttcg aggattttaa gattgagaac cnaacatcat catcctcggc    120
gttgtcggat gaatattctt cttcttcttc ttcgcccgaa tccgatatta ctttcttgga    180
tttctcggat tcttgtgaaa caacatgcaa tcttgggttg gacttggaaa agtatccttc    240
cgtggagatt gattgggcag ctttatctga gtcatgaatg atgttagtgg ttttgtcttt    300
gttgaacggt ttaatgattt gatgtgtttt aggtttttt  ttcatgtgtc ttgggcagca    360
gctgcaacga aatttttac cgttgaa                                         387
```

```
<210> SEQ ID NO 42
<211> LENGTH: 301
<212> TYPE: DNA
<213> ORGANISM: Glycine max
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 42
```

```
ccaaaatctg ctaggtgtag naaaaaaacn tgggtgcagg aagaaatcgc ctggacgtgt     60
tgagttggtc gcccacgaaa aactaacgcc agtccaatag gtcttccaac cttctcaatg    120
ggcccaaggt ccaaatcttg atgtttttaa ctcctagtgg gccttggctc acttaatcat    180
agtgtgggaa gcctaataaa nttgttattt aaaggaaaat acgatttggt tttagttgcc    240
ttttgttttg ttattttctt tgatagcaag tcaattggat gagaaggctc tgaactctga    300
a                                                                    301
```

```
<210> SEQ ID NO 43
<211> LENGTH: 301
<212> TYPE: DNA
<213> ORGANISM: Glycine max
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
```

```
<221> NAME/KEY: misc_feature
<222> LOCATION: (201)..(201)
<223> OTHER INFORMATION: n is a, c, g, or t

<400> SEQUENCE: 43
taagtagtga ctgcagcggc agtggtggng gtggtagtga aggnggcatt tagtggtttg      60
gtagcagtgg tcggtagagg tggtaatggc ggctgtgatg gcagagagag accaaaacaa     120
ggaaaacatt tatgtgatgt gggggtgatt agggattgct atttagaggg taggggttag     180
gaactgagac aagttaattt nagttgtatt gtaattccat ggaattggac tttggaatta     240
tgattccaac tctaaaaacg ttataattaa aattccaaga tccaattacc taccaaattc     300
c                                                                    301

<210> SEQ ID NO 44
<211> LENGTH: 301
<212> TYPE: DNA
<213> ORGANISM: Glycine max
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t

<400> SEQUENCE: 44
tctatgctta gtcggttcat tcatagaagc tggcattggc tacaacatgg gagagntgac      60
tgactatcac gatataataa agctagaaaa atagcaatag catgcaaatt aaatcatgaa     120
gtagataact aattctcaag atagaaaaat aatgcgaagc aaatttattg gatcttacga     180
actgtggagg caacaggcaa nagctctgga ctcaaacttt ataagagaag cagcctatat     240
tatgtttctt ggattgccaa caaacaagag aaatcaccaa ggaaaantac aaaaaccctg     300
t                                                                    301

<210> SEQ ID NO 45
<211> LENGTH: 28
<212> TYPE: DNA
<213> ORGANISM: Glycine max

<400> SEQUENCE: 45
gggtgagaaa aaggagagaa aaactaac                                        28

<210> SEQ ID NO 46
<211> LENGTH: 24
<212> TYPE: DNA
<213> ORGANISM: Glycine max

<400> SEQUENCE: 46
accccaataa agtcttccca caag                                            24

<210> SEQ ID NO 47
<211> LENGTH: 15
<212> TYPE: DNA
<213> ORGANISM: Glycine max

<400> SEQUENCE: 47
aatagtcatg caacc                                                      15
```

<210> SEQ ID NO 48
<211> LENGTH: 14
<212> TYPE: DNA
<213> ORGANISM: Glycine max

<400> SEQUENCE: 48
atagtcctgc aacc                                                     14

<210> SEQ ID NO 49
<211> LENGTH: 28
<212> TYPE: DNA
<213> ORGANISM: Glycine max

<400> SEQUENCE: 49
aactttcttt ctgcataaat actgcaaa                                      28

<210> SEQ ID NO 50
<211> LENGTH: 25
<212> TYPE: DNA
<213> ORGANISM: Glycine max

<400> SEQUENCE: 50
ggtcgtaagt atgtacccat ttgct                                         25

<210> SEQ ID NO 51
<211> LENGTH: 17
<212> TYPE: DNA
<213> ORGANISM: Glycine max

<400> SEQUENCE: 51
acgagttaag aataaaa                                                  17

<210> SEQ ID NO 52
<211> LENGTH: 15
<212> TYPE: DNA
<213> ORGANISM: Glycine max

<400> SEQUENCE: 52
cgagttgaga ataaa                                                    15

<210> SEQ ID NO 53
<211> LENGTH: 29
<212> TYPE: DNA
<213> ORGANISM: Glycine max

<400> SEQUENCE: 53
tgaaatgttt ctggcttgaa attattact                                     29

<210> SEQ ID NO 54
<211> LENGTH: 29
<212> TYPE: DNA
<213> ORGANISM: Glycine max

<400> SEQUENCE: 54
ctggaaactt gcatgagtgt aattatagt                                     29

<210> SEQ ID NO 55
<211> LENGTH: 17
<212> TYPE: DNA
<213> ORGANISM: Glycine max

<400> SEQUENCE: 55

```
catgttgtaa aggcaag                                              17

<210> SEQ ID NO 56
<211> LENGTH: 19
<212> TYPE: DNA
<213> ORGANISM: Glycine max

<400> SEQUENCE: 56
tgtaaagaca agtgttaaa                                            19

<210> SEQ ID NO 57
<211> LENGTH: 30
<212> TYPE: DNA
<213> ORGANISM: Glycine max

<400> SEQUENCE: 57
ccaagccata ctgtacaaaa ataaaaaaca                                30

<210> SEQ ID NO 58
<211> LENGTH: 25
<212> TYPE: DNA
<213> ORGANISM: Glycine max

<400> SEQUENCE: 58
accgtattta ggttgatctg ccaat                                     25

<210> SEQ ID NO 59
<211> LENGTH: 13
<212> TYPE: DNA
<213> ORGANISM: Glycine max

<400> SEQUENCE: 59
tctcccaaat gat                                                  13

<210> SEQ ID NO 60
<211> LENGTH: 14
<212> TYPE: DNA
<213> ORGANISM: Glycine max

<400> SEQUENCE: 60
ttctccctaa tgat                                                 14

<210> SEQ ID NO 61
<211> LENGTH: 24
<212> TYPE: DNA
<213> ORGANISM: Glycine max

<400> SEQUENCE: 61
catcttcacc ttgagcagtt ttgc                                      24

<210> SEQ ID NO 62
<211> LENGTH: 16
<212> TYPE: DNA
<213> ORGANISM: Glycine max

<400> SEQUENCE: 62
ccgtggccac gaggtt                                               16

<210> SEQ ID NO 63
<211> LENGTH: 19
<212> TYPE: DNA
<213> ORGANISM: Glycine max

<400> SEQUENCE: 63
```
atcaaggttt cagataaaa                                          19

<210> SEQ ID NO 64
<211> LENGTH: 16
<212> TYPE: DNA
<213> ORGANISM: Glycine max

<400> SEQUENCE: 64
aaggtttcgg ataaaa                                             16

<210> SEQ ID NO 65
<211> LENGTH: 25
<212> TYPE: DNA
<213> ORGANISM: Glycine max

<400> SEQUENCE: 65
tcactcactt gctttgacat ctgaa                                   25

<210> SEQ ID NO 66
<211> LENGTH: 22
<212> TYPE: DNA
<213> ORGANISM: Glycine max

<400> SEQUENCE: 66
cgtagaccag tccaagcttg tt                                      22

<210> SEQ ID NO 67
<211> LENGTH: 18
<212> TYPE: DNA
<213> ORGANISM: Glycine max

<400> SEQUENCE: 67
ttgtttccac gatttact                                           18

<210> SEQ ID NO 68
<211> LENGTH: 18
<212> TYPE: DNA
<213> ORGANISM: Glycine max

<400> SEQUENCE: 68
ttgtttccac gctttact                                           18

<210> SEQ ID NO 69
<211> LENGTH: 23
<212> TYPE: DNA
<213> ORGANISM: Glycine max

<400> SEQUENCE: 69
cttcaagagc cagagacaat cgt                                     23

<210> SEQ ID NO 70
<211> LENGTH: 25
<212> TYPE: DNA
<213> ORGANISM: Glycine max

<400> SEQUENCE: 70
gggaattgga gcttgagatt gtgaa                                   25

<210> SEQ ID NO 71
<211> LENGTH: 18
<212> TYPE: DNA
<213> ORGANISM: Glycine max

```
<400> SEQUENCE: 71
ttttccttca ccaaacag                                                 18

<210> SEQ ID NO 72
<211> LENGTH: 18
<212> TYPE: DNA
<213> ORGANISM: Glycine max

<400> SEQUENCE: 72
ttttccttct ccaaacag                                                 18

<210> SEQ ID NO 73
<211> LENGTH: 24
<212> TYPE: DNA
<213> ORGANISM: Glycine max

<400> SEQUENCE: 73
acgggaactg gtgtttgata gatg                                          24

<210> SEQ ID NO 74
<211> LENGTH: 30
<212> TYPE: DNA
<213> ORGANISM: Glycine max

<400> SEQUENCE: 74
ggaggaatct atatagtcac cgaaattgtc                                    30

<210> SEQ ID NO 75
<211> LENGTH: 20
<212> TYPE: DNA
<213> ORGANISM: Glycine max

<400> SEQUENCE: 75
ataacaacac cttaaataaa                                               20

<210> SEQ ID NO 76
<211> LENGTH: 17
<212> TYPE: DNA
<213> ORGANISM: Glycine max

<400> SEQUENCE: 76
acaaccccta aaataaa                                                  17
```

US 10,982,293 B2

METHODS FOR IMPROVING PLANT RESISTANCE TO SOYBEAN CYST NEMATODE AND COMPOSITIONS THEREOF

CROSS-REFERENCE TO RELATED APPLICATIONS

This application is a U.S. National Stage Application of International Application No. PCT/US2015/031547, filed on May 19, 2015, which claims the benefit of U.S. Provisional Application No. 62/000,604, filed on May 20, 2014, which is incorporated by reference in its entirety herein.

INCORPORATION OF SEQUENCE LISTING

A sequence listing is contained in the file named "P34128US01_SEQ.txt" which is 37,910 bytes in size (measured in MS-Windows) and was created on Nov. 18, 2016, comprises 76 nucleotide sequences, is provided herewith via the USPTO's EFS system and is herein incorporated by reference in its entirety.

BACKGROUND

The soybean, *Glycine max* (L.) Merril (*Glycine max* or soybean), is one of the major economic crops grown worldwide as a primary source of vegetable oil and protein (Sinclair and Backman, *Compendium of Soybean Diseases*, 3rd Ed. APS Press, St. Paul, Minn., p. 106 (1989)). The growing demand for low cholesterol and high fiber diets has also increased soybean's importance as a health food.

Soybean yields in the United States are reduced each year by diseases. High yields per hectare are critical to a farmer's profit margin, especially during periods of low prices for soybean. The financial loss caused by soybean diseases is important to rural economies and to the economies of allied industries in urban areas. The effects of these losses are eventually felt throughout the soybean market worldwide. Estimates of loss due to disease in the United States vary from year to year and by disease. From 1999 to 2002, soybean yield loss estimates were in the range of 8 million metric tons to 10 million metric tons in the United States (Wrather et al., Online. Plant Health Progress doi: 10:1094/PHP-2003-0325-01-RV). A recent three-year study done in the United States estimated that soybean cyst nematode (*Heterodera glycines*) caused annual losses of $1.286 billion (128.6 million bushels).

Soybean Cyst Nematode (SCN), *Heterodera glycines Ichinohe*, is an obligate parasite identified on soybeans in the United States in 1954 at Castle Hayne, N.C. (Winstead et al., *Plant Dis. Rep.*, 39:9-11 (1955)). Since its discovery, the SCN has been recognized as one of the most destructive pests in soybean. It has been reported in nearly all states in which soybeans are grown, and it causes major production problems in several states, being particularly destructive in the Midwestern states. See generally: Caldwell et al., *Agron. J.*, 52:635-636 (1960); Rao-Arelli and Anand, *Crop. Sci.*, 28:650-652 (1988); Baltazar and Mansur, *Soybean Genet. Newsl.*, 19:120-122 (1992); Concibido et al., *Crop Sci.* 34:240-246 (1993). For example, sensitive soybean cultivars had 5.7-35.8% lower seed yields than did resistant cultivars on SCN race-3 infested sites in Iowa (Niblack and Norton, *Plant Dis.*, 76:943-948 (1992)). Current methods for managing SCN include crop rotation with non-host crops (typically corn) to reduce SCN population densities, the use of SCN resistant cultivars to maximize yields, and more recently the rotation of the SCN resistant cultivars to minimize adaptation by the SCN population.

SCN accounts for roughly 40% of the total disease in soybean and can result in significant yield losses (up to 90%). Currently, the most cost effective control measures are crop rotation and the use of host plant resistance. While breeders have successfully developed SCN resistant soybean lines, breeding is both difficult and time consuming due to the complex and polygenic nature of resistance. The resistance is often race specific and does not provide stability over time due to changing SCN populations in the field. In addition, many of the resistant soybean varieties carry a significant yield penalty when grown in the absence of SCN.

Shortly after the discovery of SCN in the United States, sources of SCN resistance were identified (Ross and Brim, *Plant Dis. Rep.*, 41:923-924 (1957)). Some lines, such as Peking and Plant Introduction (PI) PI88788, were quickly incorporated into breeding programs. Peking became widely used as a source of resistance due to its lack of agronomically undesirable traits, with Pickett as the first SCN resistant cultivar released (Brim and Ross, *Crop Sci.*, 6:305 (1966)).

Field populations of SCN are genetically variable. In the early 1960s, researchers found that geographically distinct populations of SCN varied in their ability to reproduce on resistant soybean cultivars or plant introductions (PIs). These PIs were soybean relatives from the Orient (China, Japan, and Russia) where soybeans originated. The recognition that certain SCN resistant populations could overcome resistant cultivars led to an extensive screen for additional sources of SCN resistance. Currently there are more than 130 PIs known to have SCN resistance.

Nematologists and soybean breeders proposed calling these variable populations "races" based on a differential host test on cultivars Peking and Pickett, and two soybean plant introductions from Asia PI 88788 and 90763 (Golden et al. "Terminology and identity of infraspecific forms of the soybean cyst nematode (*Heterodera glycines*)" Plant Disease Reporter. 1970; 54:544-546). The cultivar Lee was recommended as the standard susceptible for race determination tests. Classical classifications include 16 races based on all the possible combinations on four differentials (Riggs and Schmitt, "Complete Characterization of the Race Scheme for *Heterodera glycines*" J Nematol. 1988 July; 20(3):392-5) (see Table 1).

TABLE 1

SCN Race classification

| Race | Pickett | Peking | PI 88788 | PI 90763 |
|------|---------|--------|----------|----------|
| 1  | − | − | + | − |
| 2  | + | + | + | − |
| 3  | − | − | − | − |
| 4  | + | + | + | + |
| 5  | + | − | + | − |
| 6  | + | − | − | − |
| 7  | − | − | + | + |
| 8  | − | − | − | + |
| 9  | + | + | − | − |
| 10 | + | − | − | + |
| 11 | − | + | + | − |
| 12 | − | + | − | + |
| 13 | − | + | − | − |
| 14 | + | + | − | + |

TABLE 1-continued

SCN Race classification

| Race | Pickett | Peking | PI 88788 | PI 90763 |
|------|---------|--------|----------|----------|
| 15   | +       | −      | +        | +        |
| 16   | −       | +      | +        | +        |

+ = Number or females and cysts recovered was 10% or more of the number on Lee 74 cultivar.
− = Number of females and cysts recovered was less than 10% of the number on Lee 74 cultivar.

SCN resistance or partial resistance is determined by a comparison of the plant in question with a known SCN sensitive host, Lee 74, according to the method set forth in Schmitt, *J. Nematol.* 20:392-395 (1988). In the US, SCN race 3 is considered to be the prominent race in the Midwestern soybean producing states while the prevalence of SCN race 1 is increasing. On the eastern seaboard and along areas bordering the Mississippi, SCN race 2 is prevalent. Similar shifts in SCN race prevalence is occurring in other soybean producing regions, including for example, Brazil. Therefore, it is important to develop soybean varieties that confer broad-spectrum SCN race resistance.

More recently, an alternative, the *Heterodera glycines* (HG) type classification scheme was introduced for characterizing field populations of SCN ("A Revised Classification Scheme for Genetically Diverse Populations of *Heterodera glycines*." Niblack et al. J Nematol. 2002 December; 34(4): 279-88). The HG type classification utilizes seven plant introductions (PIs) as "indicator lines," (Table 2) (Niblack, "Soybean Cyst Nematode Management Reconsidered," *Plant Diseases,* 89(10):1020-1026 (2005)), meaning that they are a suitable hosts for a given SCN population. A series of indicator numbers is then assigned to the population based upon the observed infection of the host "indicator lines." For example, an SCN race 1 population corresponds to an HG type 2.5.7 population (overcoming PI 88788, PI 209332 and Cloud). An SCN race 2 population corresponds to an HG type 1.2.5.7 (overcoming Peking, PI 88788, PI 209332 and Cloud), while an SCN race 3 population corresponds to an HG type 0 (sometimes an HG type 7, meaning it overcomes (Female index greater than 10%) either none of the indicator lines or just Cloud).

TABLE 2

HG type classification of SCN populations

| Indicator Number | Line |
|------------------|------|
| 1 | PI 548402* |
| 2 | PI 88788* |
| 3 | PI 90763* |
| 4 | PI 437654 |
| 5 | PI 209332 |
| 6 | PI 89722 |
| 7 | PI 548316 (also known as Cloud) |

*Introductions corresponding to host cultivars of original SCN race tests listed in Table 1.

SUMMARY

The present disclosure provides a method for creating a population of soybean plants with enhanced soybean cyst nematode resistance comprising:
a. providing a first population of soybean plants;
b. detecting the presence of a genetic marker that is genetically linked to a Soybean Cyst Nematode resistance locus on linkage group B1 by 20 cM or less in the first population;
c. selecting one or more soybean plants containing said marker from the first population of soybean plants; and
d. producing a population of offspring from at least one of said selected soybean plants.

The present disclosure further provides method wherein the genetic marker detected is genetically linked to the soybean cyst nematode resistance locus on linkage group B1 by less than 15 cM, more preferably less than 10 cM.

In another embodiment, the present disclosure provides detecting a genetic marker located within a chromosome interval comprising and flanked by Glyma11g33160 and BARCSOYSSR_11_1442. In a further embodiment, the present disclosure provides detecting a genetic marker located within a chromosome interval comprising and flanked by Glyma11g33490 and Glyma11g36970. In a further embodiment, the present disclosure provides detecting a genetic marker located within a chromosome interval comprising and flanked by Glyma11g33910 and Glyma11g37440. In a further embodiment, the present disclosure provides detecting a genetic marker located within a chromosome interval comprising and flanked by Glyma11g34850 and Glyma11g38050.

In a further embodiment, the present disclosure provides detecting a genetic marker located within a chromosome interval comprising and flanked by SEQ ID NO. 1 and SEQ ID NO. 44. In a further embodiment, the present disclosure provides detecting a genetic marker located within a chromosome interval comprising and flanked by SEQ ID NO. 11 and SEQ ID NO. 39. In a preferred embodiment, the genetic marker is selected from at least one of the group consisting of SEQ ID NOs. 1-44.

In accordance with this invention, the soybean cyst nematode resistance locus is derived from a Peking cultivar. In another embodiment of this invention a portion of the soybean cyst nematode is *Heterodera glycines*, race 1, 2, or 3. In particular in one embodiment of this invention a portion of the soybean cyst nematode is *Heterodera glycines* HG type 0, HG type 7, HG type 2.5.7, or HG type 1. 2.5.7.

The present disclosure also provides a method of creating a population of soybean plants comprising at least one allele associated with enhanced soybean cyst nematode resistance comprising at least one sequence selected from the group consisting of SEQ ID NO: 1 to 44, the method comprising the steps of:
a. genotyping a first population of soybean plants, said population containing at least one allele associated with enhanced soybean cyst nematode resistance, the at least one allele associated with enhanced soybean cyst nematode resistance comprising at least one sequence selected from the group consisting of SEQ ID NO: 1 to 44;
b. selecting from said first population one or more identified soybean plants containing said at least one allele associated with enhanced soybean cyst nematode resistance comprising at least one sequence selected from the group consisting of SEQ ID NO: 1 to 44; and
c. producing from said selected soybean plants a second population, thereby creating a population of soybean plants comprising at least one allele associated with enhanced soybean cyst nematode resistance comprising at least one sequence selected from the group consisting of SEQ ID NO: 1 to 44.

In one embodiment, the allele associated with enhanced soybean cyst nematode resistance is also present in the Peking cultivar.

The present disclosure further provides a method for creating a population of soybean plants with enhanced soybean cyst nematode resistance comprising:
a. providing a first population of soybean plants;
b. concurrently detecting the presence of at least one genetic marker that is genetically linked to each of rhg1, Rhg4, and rhg1d by 20 cM or less in the first population;
c. selecting one or more soybean plants containing said at least one markers from the first population of soybean plants; and
d. producing a population of offspring from at least one of said selected soybean plants.

In one embodiment, the at least one genetic marker detected is genetically linked to at least one of rhg1, Rhg4, and rhg1d by less than 15 cM. In another embodiment, the at least one genetic marker detected is genetically linked to at least one of rhg1, Rhg4, and rhg1d by less than 10 cM.

DETAILED DESCRIPTION

Figure 1:
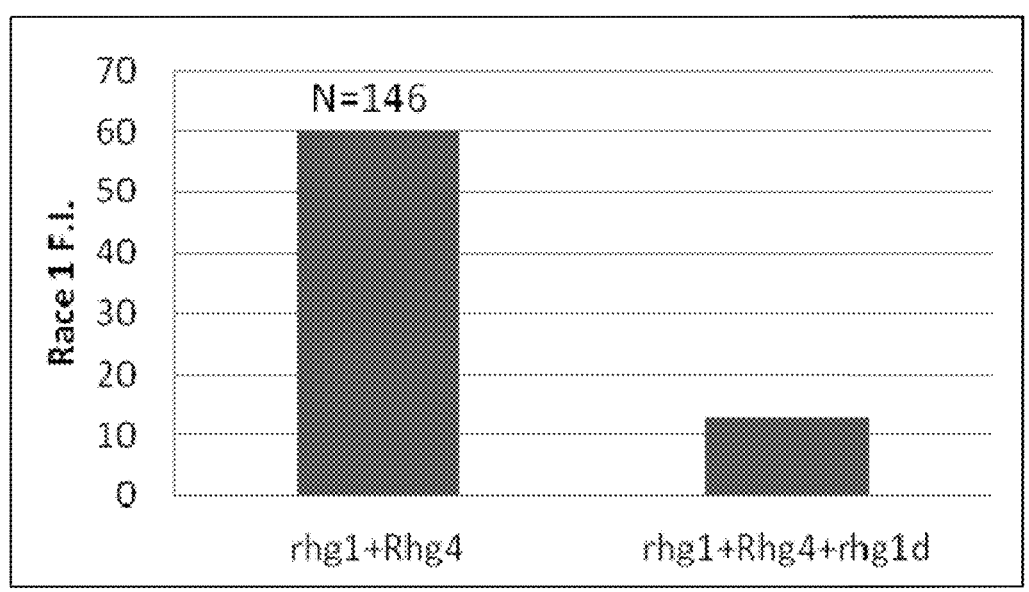
FIG. 1 shows the results of the effects of an rhg1d SCN resistance allele on the resistance of soybean to SCN race 1 according to an aspect of the present disclosure.

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties.

Concibido et al. reported that Peking provides resistance to SCN race 1 (Crop Sci. 37:258-264). However, during breeding experiments in certain backgrounds, it was discovered that race 1 resistance conferred by the Peking source is not conditioned by a 2-gene model as expected. The present disclosure has found that a third locus from Peking is required for race 1 resistance. As provided herein, this third locus appears to be a duplicate of one of the two previously known loci involved in Peking-type resistance. The present disclosure provides for varieties with Peking-type resistance. The present disclosure includes and provides for methods to introduce resistance into existing elite lines to provide for broad-spectrum SCN race resistant lines as part of an SCN management strategy. The present disclosure identifies the rhg1d locus and the rhg1d allele from Peking, provides tightly linked single nucleotide polymorphisms (SNPs) and demonstrates that the rhg1d SCN resistance allele is important for race 1 and possibly race 2 resistances.

As provided herein, Peking-type resistance can be obtained using markers which tag the Peking allele of rhg1d. Such markers can be used in early generations to select for populations with resistance, or used in later generations to characterize and prioritize which material to advance into yield testing trials. The markers provided herein also provide for the breeding of plants incorporating all known SCN resistance alleles into a single line. The present disclosure provides an expanded base of Peking-type resistant material for breeding programs, and this larger base allows agronomically acceptable and high-yielding varieties with Peking-type resistance.

Chromosome Intervals

The term "chromosome interval" designates a contiguous linear span of genomic DNA that resides in planta on a single chromosome. The term also designates any and all genomic intervals defined by any of the markers set forth in this invention. The genetic elements located on a single chromosome interval are physically linked and the size of a chromosome interval is not particularly limited. In some aspects, the genetic elements located within a single chromosome interval are genetically linked, typically with a genetic recombination distance of, for example, less than or equal to 20 cM, or alternatively, less than or equal to 10 cM. That is, two genetic elements within a single chromosome interval undergo meiotic recombination at a frequency of less than or equal to 20% or 10%, respectively.

The boundaries of a chromosome interval can be defined by genetic recombination distance or by markers. In one embodiment, the boundaries of a chromosome interval comprise markers. In another embodiment, the boundaries of a chromosome interval comprise markers that will be linked to the gene controlling the trait of interest, i.e., any marker that lies within a given interval, including the terminal markers that defining the boundaries of the interval, and that can be used as a marker for the presents or absence of disease tolerance. In one embodiment, the intervals described herein encompass marker clusters that co-segregate with disease tolerance. The clustering of markers occurs in relatively small domains on the chromosomes, indicating the presence of a genetic locus controlling the trait of interest in those chromosome regions. The interval encompasses markers that map within the interval as well as the markers that define the terminal.

An interval described by the terminal markers that define the endpoints of the interval will include the terminal markers and any marker localizing within that chromosome domain, whether those markers are currently known or unknown. Although it is anticipated that one skilled in the art may describe additional polymorphic sites at marker loci in and around the markers identified herein, any marker within the chromosome intervals described herein that are associated with disease tolerance fall within the scope of this claimed invention.

"Quantitative trait loci" or a "quantitative trait locus" (QTL) is a genetic domain that effects a phenotype that can be described in quantitative terms and can be assigned a "phenotypic value" which corresponds to a quantitative value for the phenotypic trait. A QTL can act through a single gene mechanism or by a polygenic mechanism. In some aspects, the invention provides QTL chromosome intervals, where a QTL (or multiple QTLs) that segregates with disease tolerance is contained in those intervals. In one embodiment of this invention, the boundaries of chromosome intervals are drawn to encompass markers that will be linked to one or more QTL. In other words, the chromosome interval is drawn such that any marker that lies within that interval (including the terminal markers that define the boundaries of the interval) is genetically linked to the QTL. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

In one embodiment, the present disclosure provides a plant comprising a nucleic acid molecule selected from the group consisting of SEQ ID NO: 1-44 and fragments thereof, and complements of both. In another embodiment, the present disclosure also provides a plant comprising the allele of the rhg1d chromosome interval, or fragments and complements thereof. The present disclosure also provides for any plant comprising any combination of one or more disease resistance loci linked to at least one marker selected from the group consisting of SEQ ID NOs: 1-44.

The location in the soybean genome of the rhg1d locus and the chromosome interval comprising markers closely linked to it are disclosed in Table 3. Genetic map loci are represented in cM, with position zero being the first (most distal) marker known at the beginning of the chromosome on both Monsanto's internal consensus map (MON Map) and the GmConsensus 4.0 soybean genomic map, which is freely available to the public from the Soybase(dot)org website and commonly used by those skilled in the art. Also disclosed in Table 3 are the physical locations of loci as they are reported on the Glyma1.0 public assembly by the US Department for Energy Joint Genome Institute (DOE-JGI) Community Sequencing Program (CSP), available on the phytozome(dot)net website (Schmutz J, et al. (2010). "Genome sequence of the palaeopolyploid soybean." Nature 463, 178-183).

TABLE 3

Genetic and physical map positions of markers and chromosome intervals associated with rhg1d

| | Relative Genetic Map Position | | Physical Map Position (Glyma1.0) | |
|---|---|---|---|---|
| | MON Map | GmConsensus 4.0B1 Map | | |
| Marker/Locus Name | cM† | cM† | Chr Start | Chr End |
| Glyma11g33160 | 145.3 | | 34927188 | 34933074 |
| BARCSOYSSR_11_1237 | 145.7 | | 34936244 | 34936281 |
| Glyma11g33190 | 146 | | 34961655 | 34962190 |
| Glyma11g33260 | 147.1 | | 35052372 | 35054227 |
| Glyma11g33340 | 148 | | 35129083 | 35133023 |
| Glyma11g33380 | 149 | | 35219000 | 35220745 |
| Glyma11g33490 | 150.1 | | 35302420 | 35302830 |
| Glyma11g33580 | 151 | | 35402168 | 35409237 |
| Sat_364 | 151.8 | 83.862 | 31593982 | 31594345 |
| BARCSOYSSR_11_1265 | 151.5 | | 35421738 | 35421767 |
| Glyma11g33630 | 152 | | 35479312 | 35480524 |
| BARCSOYSSR_11_1277 | 153 | | 35574196 | 35574217 |
| Glyma11g33800 | 154 | | 35658469 | 35658726 |
| Glyma11g33910 | 155.3 | | 35765400 | 35765956 |
| Glyma11g33990 | 156 | | 35826499 | 35828277 |
| Glyma11g34070 | 157 | | 35915110 | 35921087 |
| BARCSOYSSR_11_1303 | 158 | | 35998044 | 35998079 |
| Glyma11g34190 | 159 | | 36078824 | 36079498 |
| BARCSOYSSR_11_1320 | 160 | | 36173541 | 36173578 |
| Glyma11g34420 | 161 | | 36252122 | 36258553 |
| BARCSOYSSR_11_1336 | 162 | | 36346332 | 36346393 |
| Glyma11g34640 | 163 | | 36437890 | 36438358 |
| Satt665 | 164 | 91.545 | 36229108 | 36229369 |
| Glyma11g34710 | 164 | | 36521521 | 36523895 |
| Glyma11g34820 | 165 | | 36608326 | 36608450 |
| Glyma11g34850 | 165.3 | | 36632018 | 36632472 |
| SEQ ID NO. 1 | 165.3 | | 36632818 | 36633119 |
| BARCSOYSSR_11_1358 | 166 | | 36686795 | 36686822 |
| SEQ ID NO. 2 | 166 | | 36688890 | 36689191 |
| SEQ ID NO. 3 | 166.1 | | 36696378 | 36696679 |
| SEQ ID NO. 4 | 166.4 | | 36721571 | 36721872 |
| SEQ ID NO. 5 | 166.5 | | 36732918 | 36733219 |
| BARCSOYSSR_11_1367 | 167 | | 36775521 | 36775540 |
| SEQ ID NO. 6 | 167.5 | | 36823232 | 36823533 |
| Satt359 | 168 | 93.137 | 36868221 | 36868398 |
| BARCSOYSSR_11_1374 | 168 | | 36870343 | 36870370 |
| SEQ ID NO. 7 | 168.1 | | 36874451 | 36874752 |
| SEQ ID NO. 8 | 168.3 | | 36898350 | 36898651 |
| SEQ ID NO. 9 | 168.8 | | 36931482 | 36931783 |

TABLE 3-continued

Genetic and physical map positions of markers
and chromosome intervals associated with rhg1d

| | Relative Genetic Map Position | | Physical Map Position (Glyma1.0) | |
|---|---|---|---|---|
| Marker/Locus Name | MON Map cM† | GmConsensus 4.0B1 Map cM† | Chr Start | Chr End |
| SEQ ID NO. 10 | 169 | | 36955294 | 36955595 |
| Glyma11g35250 | 169 | | 36958009 | 36958362 |
| SEQ ID NO. 11 | 169.5 | | 36992666 | 36992967 |
| SEQ ID NO. 12 | 169.7 | | 37009501 | 37009802 |
| Glyma11g35380 | 170 | | 37032122 | 37033953 |
| SEQ ID NO. 13 | 170.6 | | 37092726 | 37093027 |
| SEQ ID NO. 14 | 170.8 | | 37105699 | 37106000 |
| SEQ ID NO. 15 | 170.8 | | 37114205 | 37114506 |
| Glyma11g35460 | 171 | | 37123336 | 37135322 |
| SEQ ID NO. 16 | 171 | | 37129711 | 37130012 |
| SEQ ID NO. 17 | 171.1 | | 37139959 | 37140260 |
| SEQ ID NO. 18 | 171.2 | | 37149060 | 37149361 |
| Sat_123 | 171.3 | 96.149 | 36660412 | 36660685 |
| SEQ ID NO. 19 | 171.3 | | 37152558 | 37152859 |
| SEQ ID NO. 20 | 171.6 | | 37179389 | 37179690 |
| BARCSOYSSR_11_1397 | 172 | | 37218015 | 37218042 |
| SEQ ID NO. 21 | 172 | | 37219747 | 37220048 |
| SEQ ID NO. 22 | 172.1 | | 37224311 | 37224612 |
| SEQ ID NO. 23 | 172.2 | | 37237162 | 37237463 |
| SEQ ID NO. 24 | 172.3 | | 37240055 | 37240356 |
| SEQ ID NO. 25 | 173 | | 37299645 | 37299946 |
| BARCSOYSSR_11_1405 | 173 | | 37299897 | 37299916 |
| SEQ ID NO. 26 | 173.2 | | 37316512 | 37316813 |
| SEQ ID NO. 27 | 173.3 | | 37329191 | 37329492 |
| SEQ ID NO. 28 | 173.7 | | 37363682 | 37363330 |
| SEQ ID NO. 29 | 173.8 | | 37378288 | 37378589 |
| SEQ ID NO. 30 | 173.9 | | 37395686 | 37395987 |
| Glyma11g35800 | 174 | | 37405137 | 37406128 |
| SEQ ID NO. 31 | 174 | | 37410978 | 37411279 |
| SEQ ID NO. 32 | 174.2 | | 37439158 | 37439459 |
| SEQ ID NO. 33 | 174.2 | | 37434907 | 37435690 |
| SEQ ID NO. 34 | 174.3 | | 37457650 | 37457951 |
| SEQ ID NO. 35 | 174.4 | | 37465895 | 37466196 |
| SEQ ID NO. 36 | 174.6 | | 37484430 | 37484731 |
| SEQ ID NO. 37 | 174.7 | | 37490068 | 37490369 |
| SEQ ID NO. 38 | 174.7 | | ** | ** |
| SEQ ID NO. 39 | 174.8 | | 37498095 | 37498396 |
| Glyma11g35930 | 175 | | 37500291 | 37503485 |
| Glyma11g36080 | 176 | | 37618529 | 37620757 |
| SEQ ID NO. 40 | 176.3 | | 37638042 | 37638343 |
| Glyma11g36160 | 177 | | 37702297 | 37705904 |
| SEQ ID NO. 41 | 178 | | ** | ** |
| Glyma11g36300 | 178 | | 37803519 | 37804943 |
| SEQ ID NO. 42 | 178.6 | | 37851827 | 37852128 |
| Glyma11g38170 | 179 | | 37886841 | 37885165 |
| SEQ ID NO. 43 | 179.1 | | 37898653 | 37898954 |
| Glyma11g38060 | 179.9 | | 37985715 | 37977678 |
| SEQ ID NO. 44 | 180 | | 37987955 | 37988256 |
| Glyma11g38050 | 180 | | 37990945 | 37990130 |
| BARCSOYSSR_11_1496 | 181 | | 38060511 | 38060490 |
| BARCSOYSSR_11_1494 | 182.2 | | 38086139 | 38086110 |
| BARCSOYSSR_11_1489 | 183 | | 38114498 | 38114455 |
| Glyma11g37840 | 183.8 | | 38152213 | 38151246 |
| Glyma11g37830 | 184.2 | | 38170644 | 38169015 |
| Glyma11g37760 | 185 | | 38214844 | 38209385 |
| BARCSOYSSR_11_1486 | 186 | | 38257803 | 38257778 |
| Satt484 | 186.8 | | 38291580 | 38291278 |
| Glyma11g37650 | 187 | | 38304078 | 38297532 |
| BARCSOYSSR_11_1480 | 188 | | 38353004 | 38352979 |
| Glyma11g37510 | 189 | | 38398036 | 38395801 |
| Glyma11g37440 | 190 | | 38447028 | 38443099 |
| Glyma11g37380 | 191 | | 38488009 | 38485869 |
| Glyma11g37310 | 192 | | 38530830 | 38527805 |
| Glyma11g37260 | 193 | | 38573620 | 38571357 |
| Sat_331 | 193.3 | 110.731 | 38622733 | 38622467 |
| Satt453 | 193.5 | 108.409 | 38639035 | 38638802 |
| Glyma11g37090 | 194 | | 38679155 | 38673792 |
| Glyma11g36970 | 195 | | 38754990 | 38754587 |
| Glyma11g36830 | 196 | | 38849316 | 38845284 |
| Glyma11g36680 | 197 | | 38944710 | 38942836 |

TABLE 3-continued

Genetic and physical map positions of markers
and chromosome intervals associated with rhg1d

| | Relative Genetic Map Position | | Physical Map Position (Glyma1.0) | |
|---|---|---|---|---|
| | MON Map | GmConsensus 4.0B1 Map | | |
| Marker/Locus Name | cM† | cM† | Chr Start | Chr End |
| Glyma11g36410 | 198 | | 39089896 | 39088423 |
| BARCSOYSSR_11_1442 | 199 | | 39143566 | 39143547 |

†cM = centiMorgans;
** Exact coordinates not known.
Coordinates can be estimated based on the nearest flanking loci with known coordinates.

In Table 3, "cM" refers to the classical definition of a centimorgan (Haldane 1919 J Genet 8:299-309) wherein one cM is equal to a 1% chance that a trait at one genetic locus will be separated from a trait at another locus due to crossing over in a single meiosis (meaning the traits cosegregate 99% of the time), and this definition is used herein to delineate map locations pertaining to this invention.

For example, the rhg1d chromosome interval located on LG B1 contains SEQ ID NOs. 1-44 and is flanked by the markers Glyma11g34850 and Glyma11g38050, which are separated by approximately 15 cM on the internally-derived genetic map. This chromosome interval encompasses a marker cluster that co-segregates with SCN resistance in the populations studied at a −Log 10 (P value)≥3.0. An example of a subinterval of the rhg1d chromosome interval is that which is flanked by SEQ ID NO. 1 and SEQ ID NO. 44, separated by approximately 15 cM on the internally-derived genetic map, that define a chromosome interval encompassing a cluster of markers that co-segregate with SCN resistance in the populations studied at a −Log 10(P value)≥3.0.

Thus, one skilled in the art can use this invention to improve the efficiency of breeding for improved disease tolerance in soybean by associating disease tolerance phenotypes with genotypes at previously unknown disease tolerance loci in the soybean genome. Disclosed herein are chromosome interval that comprise alleles responsible for phenotypic differences between disease tolerant and disease susceptible soybean lines. Example chromosome intervals are characterized by the genomic regions including and flanked by and including the markers Glyma11g34850 and Glyma11g38050 on chromosome B1, and comprise markers within or closely linked to (within 20 cM of) the rhg1d locus. This invention also comprises other intervals whose borders fall between, and including, those of Glyma11g33160 and BARCSOYSSR_11_1442, or any interval closely linked to those intervals.

Examples of markers useful for this purpose comprise the SNP markers listed in Table 3, or any marker that maps within the chromosome intervals described herein (including the termini of the intervals), or any marker linked to those markers. Such markers can be assayed simultaneously or sequentially in a single sample or population of samples.

Accordingly, the markers and methods of the present disclosure can be utilized to guide MAS or breeding soybean varieties with the desired complement (set) of allelic forms of chromosome intervals associated with superior agronomic performance (tolerance, along with any other available markers for yield, disease resistance, etc.). Any of the disclosed marker alleles can be introduced into a soybean line via introgression, by traditional breeding (or introduced via transformation, or both) to yield a soybean plant with superior agronomic performance. The number of alleles associated with tolerance that can be introduced or be present in a soybean plant of the present disclosure ranges from one to the number of alleles disclosed herein, each integer of which is incorporated herein as if explicitly recited.

Marker-assisted selection (MAS) using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein could be useful and within the scope of this invention.

Similarly, by identifying plants lacking the desired marker locus, susceptible or less tolerant plants can be identified, and, e.g., eliminated from subsequent crosses. Similarly, these marker loci can be introgressed into any desired genomic background, germplasm, plant, line, variety, etc., as part of an overall MAS breeding program designed to enhance yield. The invention also provides chromosome QTL intervals that find equal use in MAS to select plants that demonstrate disease tolerance or improved tolerance. Similarly, the QTL intervals can also be used to counter-select plants that are susceptible or have reduced tolerance to disease.

In some embodiments, the present disclosure provides methods for selecting a soybean plant with enhanced SCN resistance. These methods comprise detecting an SCN resistant allele at a polymorphic locus in a chromosomal segment flanked by any two of marker loci listed in Table 3. In other embodiments, these methods comprise detecting an SCN resistant allele at a polymorphic locus in a chromosomal segment flanked by any two of marker loci SEQ ID Nos. 1-44. In further embodiments, these methods comprise detecting an SCN resistant haplotype in a chromosomal segment flanked by any two of marker loci SEQ ID Nos. 1-44. In other embodiments, these methods comprise detecting an SCN resistant allele at a polymorphic locus in a chromosomal segment flanked by any two of marker loci SEQ ID Nos. 11-44. In further embodiments, these methods comprise detecting an SCN resistant haplotype in a chromosomal segment flanked by any two of marker loci SEQ ID Nos. 11-44. In other embodiments, these methods comprise detecting an SCN resistant allele at a polymorphic locus in a chromosomal segment flanked by any two of marker loci SEQ ID Nos. 11-39. In further embodiments, these methods comprise detecting an SCN resistant haplotype in a chromosomal segment flanked by any two of marker loci SEQ ID Nos. 11-39.

The present disclosure also extends to a method of making a progeny soybean plant. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant of the present disclosure in that it comprises at least one of the allelic forms of the markers of the present disclosure, such that the progeny are capable of inheriting the allele.

Often, a method of the present disclosure is applied to at least one related soybean plant such as from progenitor or descendant lines in the subject soybean plants' pedigree such that inheritance of the desired tolerance allele can be traced. The number of generations separating the soybean plants being subject to the methods of the present disclosure will generally be from 1 to 20, commonly 1 to 5, and typically 1, 2, or 3 generations of separation, and quite often a direct descendant or parent of the soybean plant will be subject to the method (i.e., one generation of separation).

Thus, with this invention, one skilled in the art can detect the presence or absence of disease tolerance genotypes in the genomes of soybean plants as part of a marker assisted selection program. In one embodiment, a breeder ascertains the genotype at one or more markers for a disease tolerant parent, which contains a disease tolerance allele, and the genotype at one or more markers for a susceptible parent, which lacks the tolerance allele. For example, the markers of the present disclosure can be used in MAS in crosses involving elite x exotic soybean lines by subjecting the segregating progeny to MAS to maintain disease tolerance alleles, or alleles associated with yield under disease conditions. A breeder can then reliably track the inheritance of the tolerance alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the disease tolerant parent can be reliably predicted to express the tolerant phenotype; progeny that share genotypes with the disease susceptible parent can be reliably predicted to express the susceptible phenotype. Thus, the laborious and inefficient process of manually phenotyping the progeny for disease resistance is avoided.

By providing the positions in the soybean genome of the intervals and the disease tolerance associated markers within, this invention also allows one skilled in the art to identify other markers within the intervals disclosed herein or linked to the chromosome intervals disclosed herein.

Closely linked markers flanking the locus of interest that have alleles in linkage disequilibrium with a resistance allele at that locus may be effectively used to select for progeny plants with enhanced tolerance to disease conditions. Thus, the markers described herein, such as those listed in Table 3, as well as other markers genetically or physically mapped to the same chromosome interval, may be used to select for soybean plants with enhanced tolerance to disease conditions. Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. In an introgression program, this allows for selection of the gene or locus genotype at the more proximal polymorphic markers and selection for the recurrent parent genotype at the more distal polymorphic markers.

The choice of markers actually used to practice this invention is not particularly limited and can be any marker that maps within the rhg1d chromosome intervals described herein, any marker closely linked (within 20 cM) to a marker in the rhg1d chromosome interval, or any marker selected from SEQ ID NOs: 1-44, or the markers listed in Table 3. Furthermore, since there are many different types of marker detection assays known in the art, it is not intended that the type of marker detection assay (e.g. RAPDs, RFLPs, SNPs, AFLPs, etc.) used to practice this invention be limited in any way.

Additional genetic markers can be used either in conjunction with the markers provided in Table 3 or independently of the markers provided in Table 3 to practice the methods of the instant invention. Publicly available marker databases from which useful markers can be obtained include, but are not limited to, the soybase(dot)org website on the internet (World Wide Web) that is administered by the United States Agricultural Research Service, the United States Department of Agriculture, and Iowa State University. Additional soybean markers that can be used and that have been described in the literature include, but are not limited to, Hyten et al., BMC Genomics. 11:38, 2010; Choi et al., Genetics. 176(1):685-96, 2007; Yoon et al., Theor Appl Genet. 2007 March; 114(5):885-99; and Hyten et al. Crop Sci. 2010 50: 960-968.

Sequences for SEQ ID NO. 1-44 in Table 3 can be obtained from the Sequence Listing. Sequences for the publically available markers disclosed in Table 3 can be obtained on the World Wide Web (or Internet) using the identifiers provided in Column 1 (Marker/Locus Name) from the following internet locations:

a. "soybase(dot)org" (described in Grant et al., Nucleic Acids Research, 2010, Vol. 38, Database issue D843-D846) or soybase(dot)org/gbrowse/cgi-bin/gbrows/gmax1.01/(see Hyten D L, Choi I-Y, Song Q, Specht J E, Carter T E et al. (2010) "A high density integrated genetic linkage map of soybean and the development of a 1,536 Universal Soy Linkage Panel for QTL mapping." Crop Science 50:960-968; and Hyten D L, Cannon S B, Song Q, Weeks N, Fickus E W et al. (2010). "High-throughput SNP discovery through deep resequencing of a reduced representation library to anchor and orient scaffolds in the soybean whole genome sequence." BMC Genomics 11(1):38).

b. "phytozome(dot)net" or "phytozome(dot)net/cgi-bin/gbrowse/soybean/";

c. "www(dot)plantgdb(dot)org" or "plantgdb(dot)org/GmGDB/(Assembly version Glyrna1 0.170 (April 2009)"; and, d. "ncbi(dot)nlm(dot)nih(dot)gov/sites/entrez" and subsites "ncbi(dot)nlm(dot)nih (dot)gov/nucest", "ncbi(dot)nlm(dot)nih(dot)gov/dbEST", "ncbi(dot)nlm(dot)nih(dot)

gov/genbank/", "ncbi(dot)nlm(dot)nih(dot)gov/sites/genome", "ncbi(dot)nlm(dot)nih(dot)gov/unigene", and "ncbi(dot)nlm(dot)nih(dot)gov/UniGene/UGOrg.cgi?TAXID=3847".

Molecular Genetic Markers

As used herein, "marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

As used herein, "marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., disease tolerance). As used herein, a QTL marker has a minimum of one favorable allele, although it is possible that the marker might have two or more favorable alleles found in the population. Any favorable allele of that marker can be used advantageously for the identification and construction of disease tolerant plant lines. Optionally, one, two, three or more favorable allele(s) of different markers are identified in, or introgressed into a plant, and can be selected for or against during MAS. Desirably, plants or germplasm are identified that have at least one such favorable allele that positively correlates with disease tolerance or improved disease tolerance. Alternatively, a marker allele that co-segregates with disease susceptibility also finds use with the invention, since that allele can be used to identify and counter select disease susceptible plants. Such an allele can be used for exclusionary purposes during breeding to identify alleles that negatively correlate with tolerance, to eliminate susceptible plants or germplasm from subsequent rounds of breeding. In the present disclosure, favorable alleles confer SCN resistance. The favorable alleles conferring resistance to SCN may be referred to as "resistance alleles."

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of anyone particular marker) on the basis of polynucleotide length and/or sequence. A large number of soybean molecular markers are known in the art, and are published or available from various sources, such as the soybase(dot)org internet resource. In general, any differentially inherited polymorphic trait (including a nucleic acid polymorphism) that segregates among progeny is a potential genetic marker.

In some embodiments of the disclosure, one or more marker alleles are selected for in a single plant or a population of plants. In these methods, plants are selected that contain favorable alleles from more than one tolerance marker, or alternatively, favorable alleles from more than one tolerance marker are introgressed into a desired germplasm. One of skill recognizes that the identification of favorable marker alleles is germplasm-specific. The determination of which marker alleles correlate with tolerance (or susceptibility) is determined for the particular germplasm under study. One of skill recognizes that methods for identifying the favorable alleles are known in the art. Identification and use of such favorable alleles is within the scope of this invention. Furthermore still, identification of favorable marker alleles in plant populations other than the populations used or described herein is within the scope of this invention.

Marker Detection

In some aspects, methods of the disclosure utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is an SNP type marker, and the detected allele is a SNP allele, and the method of detection is allele specific hybridization (ASH).

In general, the majority of genetic markers rely on one or more property of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present disclosure. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST®, or even simple word processors.

While the exemplary markers provided in the figures and tables herein are either SNP markers, any of the aforementioned marker types can be employed in the context of the disclosure to identify chromosome intervals encompassing genetic element that contribute to superior agronomic performance (e.g., disease tolerance or improved disease tolerance).

Primers and Probes

In general, synthetic methods for making oligonucleotides, including probes, primers, molecular beacons, PNAs, LNAs (locked nucleic acids), etc., are known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the disclosure. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon.

It is not intended that the nucleic acid probes of the disclosure be limited to any particular size.

In some preferred embodiments, the molecular markers of the disclosure are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the disclosure are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the disclosure be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present disclosure.

Linkage Analysis and QTL

Linkage Analysis

"Linkage", or "genetic linkage," is used to describe the degree with which one marker locus is "associated with" another marker locus or some other locus (for example, a tolerance locus). For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium (LD) with the tolerance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present disclosure is not limited to this particular standard, and an acceptable probability can be any probability of less than 50% (p<0.5). For example, a significant probability can be less than 0.25, less than 0.20, less than 0.15, or less than 0.1 The phrase "closely linked," in the present application, means that recombination between two linked loci occurs with a frequency of equal to or less than about 10% (i.e., are separated on a genetic map by not more than 10 cM). In one aspect, any marker of the disclosure is linked (genetically and physically) to any other marker that is at or less than 50 cM distant. In another aspect, any marker of the disclosure is closely linked (genetically and physically) to any other marker that is in close proximity, e.g., at or less than 10 cM distant. Two closely linked markers on the same chromosome can be positioned 20, 19, 18, 17, 16, 15, 14, 13, 12, 11, 10, 9, 8, 7, 6, 5, 4, 3, 2, 1, 0.75, 0.5 or 0.25 cM or less from each other.

Classical linkage analysis can be thought of as a statistical description of the relative frequencies of co-segregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate. This can be expressed as a percentage of cosegregation (recombination frequency) or, also commonly, in centiMorgans (cM).

Linkage analysis is used to determine which polymorphic marker allele demonstrates a statistical likelihood of co-segregation with the tolerance phenotype (thus, a "tolerance marker allele"). Following identification of a marker allele for co-segregation with the tolerance phenotype, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present disclosure, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

Quantitative Trait Loci

An allele of a QTL can comprise multiple genes or other genetic factors even within a contiguous genomic region or linkage group, such as a haplotype. As used herein, an allele of a disease resistance locus can encompass more than one gene or nucleotide sequence where each individual gene or nucleotide sequence is also capable of exhibiting allelic variation and where each gene or nucleotide sequence is also capable of eliciting a phenotypic effect on the quantitative trait in question. In an aspect of the present disclosure the allele of a QTL comprises one or more genes or nucleic acid sequences that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. When all the alleles present at a given locus on a chromosome are the same, that plant is homozygous at that locus. If the alleles present at a given locus on a chromosome differ, that plant is heterozygous at that locus. Plants of the present disclosure may be homozygous or heterozygous at any particular disease locus or for a particular polymorphic marker.

The principles of QTL analysis and statistical methods for calculating linkage between markers and useful QTL, or between any loci in a genome are well known in the art. Exemplary methods include penalized regression analysis, ridge regression, single point marker analysis, complex pedigree analysis, Bayesian MCMC, identity-by-descent analysis, interval mapping, composite interval mapping, and Haseman-Elston regression. QTL analyses are often performed with the help of a computer and specialized software available from a variety of public and commercial sources known to those of skill in the art.

In some embodiments of the present disclosure, a "LOD score" is used to indicate the likelihood that a marker is associated with a QTL. The LOD score essentially expresses how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, Genetics, 121:185-199 (1989), and further described by Arús and Moreno-González, Plant Breeding, Hayward, Bosemark, Romagosa (eds.) Chapman & Hall, London, pp. 314-331 (1993). A $\log_{10}$ of an odds ratio (LOD) is calculated as: LOD=$\log_{10}$ (MLE for the presence of a QTL (MLE given no linked QTL)), where MLE is a maximum likelihood estimate. As used herein, a nucleic acid marker is genetically linked to a QTL, where the marker nucleic acid molecule exhibits a LOD score of greater than 2.0, as judged by interval mapping, for SCN resistance or partial resistance, preferably where the marker nucleic acid molecule exhibits a LOD score of greater than 3.0, as judged by interval mapping, for SCN resistance or partial resistance, more preferably where the marker nucleic acid molecule exhibits a LOD score of greater than 3.5, as judged by interval mapping, for SCN resistance or partial resistance, and even more preferably where the marker nucleic acid molecule exhibits a LOD score of about 4.0, as judged by interval mapping, for SCN resistance or partial resistance based on maximum likelihood methods described by Lander and Botstein, *Genetics*, 121:185-199 (1989), and implemented in the software package MAPMAKER/QTL (default parameters) (Lincoln and Lander, *Mapping Genes Controlling Quantitative Traits Using MAPMAKER/QTL*, Whitehead Institute for Biomedical Research, Massachusetts (1990)).

Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM). In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through Marker assisted selection (MAS), a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with the disease tolerance phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

In one aspect, the present disclosure provides chromosome intervals, marker loci, germplasm for conducting genome-wide association mapping for SCN resistance. Exemplary chromosome intervals and marker loci are provided in Table 3. Smaller intervals defined by any two marker loci disclosed in Table are also contemplated. Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable soybean genetic map (for example, a composite map) can be used to help observe distribution of the identified QTL markers and/or QTL marker clustering using previously determined map locations of the markers.

Marker Assisted Selection, Plant Breeding, and Genomic Introgression

Marker-Assisted Selection

"Introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that are tolerant, exhibit improved tolerance or are susceptible to SCN infection by identifying plants having a specified allele that is linked to rhg1d.

In general, MAS uses polymorphic markers that have been identified as having a significant likelihood of co-segregation with a tolerance trait. Such markers are presumed to map near a gene or genes that give the plant its tolerance phenotype, and are considered indicators for the desired trait, and are termed QTL markers. Plants are tested for the presence or absence of a desired allele in the QTL marker.

Identification of plants or germplasm that include a marker locus or marker loci linked to a tolerance trait or traits provides a basis for performing marker assisted selection. Plants that comprise favorable markers or favorable alleles are selected for, while plants that comprise markers or alleles that are negatively correlated with tolerance can be selected against. Desired markers and/or alleles can be introgressed into plants having a desired (e.g., elite or exotic) genetic background to produce an introgressed tolerant plant or germplasm. In some aspects, it is contemplated that a plurality of tolerance markers are sequentially or simultaneously selected and/or introgressed. The combinations of tolerance markers that are selected for in a single plant is not limited, and can include any combination of markers disclosed herein or any marker linked to the markers disclosed herein, or any markers located within the QTL intervals defined herein.

In some embodiments, the allele that is detected is a favorable allele that positively correlates with disease tolerance or improved disease tolerance. In the case where more than one marker is selected, an allele is selected for each of the markers; thus, two or more alleles are selected. In some embodiments, it can be the case that a marker locus will have more than one advantageous allele, and in that case, either allele can be selected. It will be appreciated that the ability to identify QTL marker loci alleles that correlate with tolerance, improved tolerance or susceptibility of a soybean plant to disease conditions provides a method for selecting plants that have favorable marker loci as well. That is, any plant that is identified as comprising a desired marker locus (e.g., a marker allele that positively correlates with tolerance) can be selected for, while plants that lack the locus, or that have a locus that negatively correlates with tolerance, can be selected against.

In some embodiments, a disease tolerant first soybean plant or germplasm (the donor) can be crossed with a second soybean plant or germplasm (the recipient, e.g., an elite or exotic soybean, depending on characteristics that are desired in the progeny) to create an introgressed soybean plant or germplasm as part of a breeding program designed to improve disease tolerance of the recipient soybean plant or germplasm. In some aspects, the recipient plant can also contain one or more disease tolerant loci, which can be qualitative or quantitative trait loci. In another aspect, the recipient plant can contain a transgene.

In some embodiments, the recipient soybean plant or germplasm will typically display reduced tolerance to disease conditions as compared to the first soybean plant or germplasm, while the introgressed soybean plant or germplasm will display an increased tolerance to disease conditions as compared to the second plant or germplasm. An introgressed soybean plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one or multiple traits, e.g., multiple loci involved in tolerance, or multiple loci each involved in tolerance or resistance to different diseases, the efficiency of MAS compared to phenotypic screening becomes even greater, because all of the loci can be evaluated in the lab together from a single sample of DNA.

Marker-Assisted Backcrossing

One application of MAS is to use the tolerance or improved tolerance markers to increase the efficiency of an introgression effort aimed at introducing a tolerance QTL into a desired (typically high yielding) background. If the nucleic acids from a plant are positive for a desired genetic marker allele, the plant can be self-fertilized to create a true breeding line with the same genotype, or it can be crossed with a plant with the same marker or with other characteristics to create a sexually crossed hybrid generation.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding line). The more cycles of back crossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait such as tolerance to SCN infection.

Moreover, in another aspect, while maintaining the introduced markers associated with resistance, the genetic contribution of the plant providing disease resistance can be reduced by back-crossing or other suitable approaches. In one aspect, the nuclear genetic material derived from the donor material in the plant can be less than or about 50%, less than or about 25%, less than or about 13%, less than or about 5%, 3%, 2% or 1%, but that the recipient remains resistant to disease.

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

Tri-Genic Model for SCN Resistance

Figure 2:
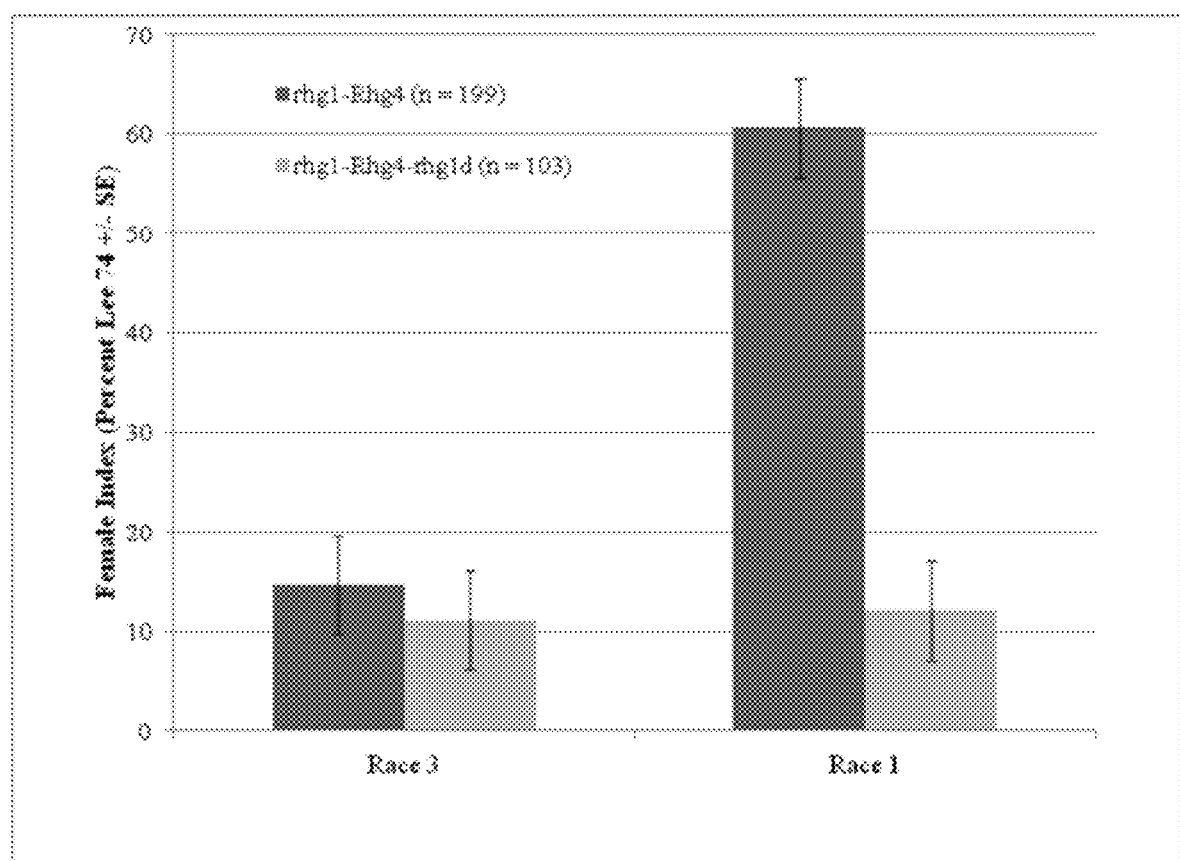
FIG. 2 shows the effects of an rhg1d SCN resistance allele on the resistance of soybean to SCN race 1 compared to SCN race 3 resistance according to an aspect of the present disclosure.

As noted in the 2004 review article by Concibido et al., (CropSci. 44:1121-1131) the majority of QTL mapping studies for the SCN resistance trait have identified the rhg1 and Rhg4 regions of linkage groups G and A2, respectively as contributing most significantly to the SCN resistance phenotype. The two loci are reported as explaining over 98% of SCN resistance (Meksem et al. (2001) TAG 103(5):710-717). Recognizing this, two groups have cloned candidate genes within the two regions (Hauge et al. 2001; Lightfoot and Meksem, 2002). Most of the studies cited by Concibido et al. 2004 were done using SCN race 3, but the same has been found to be true for SCN race 1 (Guo et al. 2006). Here for the first time, we report that for SCN race 1 resistance, three loci are required: rhg1, Rhg4, and rhg1d (FIGS. 1 and 2). The rhg1d locus is located on linkage group B1. Based on comparisons of fingerprint data between genomic regions of soybean lines that are race 1 resistant and lines that are race 1 susceptible, a matching co-segregation pattern emerged at the rhg1d locus. Further analysis reveals that the region includes a duplication of a region of the rhg1 allele. Hence, we have called the new locus rhg1d. While SCN race 1 resistant lines may have been previously produced using the rhg1 and Rhg4 loci, breeders have not been able to maintain SCN race 1 resistance. The present disclosure enables breeders to maintain race 1 resistance by tracking the presence of the rhg1d locus in combination with the previously-described rhg1 and Rhg4 loci.

The present disclosure includes and provides for a method of producing soybean plants resistant to SCN using molecular markers to select for one or more soybean plants containing at least one marker from each of rhg1, Rhg4, and rhg1d. Markers that are genetically linked to and can be used for selection of the rhg1 and Rhg4 loci are well-known in the art. Markers that are genetically linked to the rhg1d locus are described herein (Table 3).

In some embodiments, the present disclosure provides methods for creating a population of soybean plants that are resistant or moderately resistant to at least one of races 1 to 16 of SCN, which methods comprise: (a) detecting in a first population of soybean plants or seeds the presence of at least one marker allele that is genetically linked to and within about 20, 15, 10, 5, 2.5, 1, 0.5, 0.25 cM of each of rhg1, Rhg4, and rhg1d SCN resistance loci; (b) selecting a soybean plant or seed containing the genetically linked marker alleles; and (c) producing a population of offspring from the selected soybean plant or seed. In some embodiments, the detection of the marker allele genetically linked to each of rhg1, Rhg4, and rhg1d SCN resistance loci is performed concurrently, e.g., in a multiplexed reaction. In other embodiments, the detection of the marker allele genetically linked to each of rhg1, Rhg4, and rhg1d SCN resistance loci is performed separately, e.g., in separate reaction.

In some embodiments of the disclosure, the method enables production of plants resistant to SCN race 1. In some embodiments of the disclosure, the method enables production of plants resistant to SCN race 3. In some embodiments of the disclosure, the method enables production of plants resistant to SCN race 2. In a preferred embodiment of the disclosure, the source of SCN resistance is Peking-derived.

Enhancing SCN Resistance in Moderately-Resistant Soybean Germplasm Using 3-phenyl-5-(thiophen-2-yl)-1,2,4-oxadiazole As illustrated by the comprehensive review of the many QTL associated with SCN resistance and their specificity to SCN races, one of skill in the art can appreciate the complexity associated with controlling SCN infection. While breeders have successfully developed SCN resistant soybean lines, breeding is both difficult and time consuming due to the complex and polygenic nature of resistance. The resistance is often race specific and does not provide stability over time due to changing SCN populations in the field. In addition, many of the resistant soybean varieties carry a significant yield penalty when grown in the absence of SCN. There thus exists a need for methods where the SCN resistance of a given soybean germplasm is improved.

Provided herein are methods for further improving yield and/or resistance of certain soybean germplasm to SCN. In particular, it has been found that that the yield and/or SCN resistance of certain transgenic and non-transgenic soybean germplasm that exhibit some level of SCN resistance can be further enhanced by use of 3,5-disubstituted-1,2,4-oxadiazole compounds. In some embodiments, such improvements can comprise increased levels of resistance to an SCN race in soybean germplasm that is susceptible to the SCN race. In some embodiments, soybean germplasm derived from PI88788 that exhibit Race 3 SCN resistance but only negligible to moderate Race 1 SCN resistance can exhibit unexpected increases in Race 1 SCN resistance when treated with 3,5-disubstituted-1,2,4-oxadiazole compounds that exceed Race 1 SCN resistance conferred by the compounds alone. As used herein, the phrase "3,5-disubstituted-1,2,4-oxadiazole compound" refers to a compound of the formula:

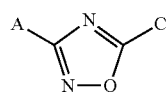

(I)

wherein A and C are aryl groups, each of which can be independently substituted with one or more substituents, and salts thereof.

As used herein, the phrases "Soybean Cyst Nematode resistant germplasm" and "SCN resistant germplasm" refer to soybean plants that comprise either a transgene that confers at least moderate SCN resistance to at least one SCN race or endogenous chromosomal loci that confer at least moderate SCN resistance to at least one SCN race.

In some embodiments, the SCN resistant germplasm used in the methods provided herein comprises haplotypes associated with SCN resistance. Such haplotypes are found in soybean germplasm including, but not limited to, Peking, PI88788, PI437654, and derivatives thereof. Such soybean germplasm are readily identified by subjecting the germplasm to infection by various SCN races and scoring for the levels of observed SCN resistance.

Generally, the methods used herein comprise treatment of soybean plants, soybean seeds, or soil used to grow soybeans with a 3,5-disubstituted-1,2,4-oxadiazole compound. Exemplary 3,5-disubstituted-1,2,4-oxadiazole of Formula (Ia) or (Ib) and salts thereof that can be used include compounds of the formulas

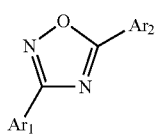

(IIa)

(IIb)

wherein $Ar_1$ is phenyl, pyridyl, pyrazyl, oxazolyl or isoxazolyl, each of which can be optionally independently substituted with one or more substituents. In one embodiment $Ar_1$ is optionally independently substituted with one or more substituents selected from the group consisting of alkyl, haloalkyl, alkoxy, haloalkoxy, halogen, acyl, ester, and nitrile each of which can be optionally independently substituted. In one embodiment, $Ar_1$ is optionally independently substituted with one or more substituents selected from the group consisting of halogen, $CF_3$, $CH_3$, $OCF_3$, $OCH_3$, CN and C(H)O. In certain embodiments, $Ar_2$ is thienyl, furanyl, oxazolyl, isoxazolyl, or phenyl each of which can be optionally independently substituted. In one embodiment, $Ar_2$ is optionally independently substituted with one or more substituents selected from the group consisting of fluorine, chlorine, $CH_3$, and $OCF_3$. In some embodiments, $Ar_1$ is unsubstituted phenyl. In other embodiments, $Ar_1$ is monosubstituted phenyl wherein the substituent is a halogen. In still other embodiments, $Ar_1$ is a disubstituted chloroalkylphenyl. In some embodiments, $Ar_2$ is substituted thienyl or substituted furanyl. In some embodiments, $Ar_2$ is unsubstituted thienyl or unsubstituted furanyl.

In some embodiments, the 3,5-disubstituted-1,2,4-oxadiazole is a compound of Formula (III) or a salt thereof,

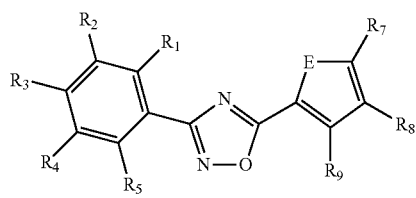

(III)

wherein $R_1$ and $R_5$ are independently selected from hydrogen, $CH_3$, F, Cl, Br, $CF_3$ and $OCF_3$; $R_2$ and $R_4$ are independently selected from hydrogen, F, Cl, Br, and $CF_3$; $R_3$ is selected from hydrogen, $CH_3$, $CF_3$, F, Cl, Br, $OCF_3$, $OCH_3$, CN, and C(H)O; $R_7$ and $R_8$ are independently selected from hydrogen and fluorine; $R_9$ is selected from hydrogen, F, Cl, $CH_3$, and $OCF_3$; and E is O, N or S. Methods for making the 3,5-disubstituted-1,2,4-oxadiazole are disclosed in US Patent Publication US 20090048311 and co-assigned U.S. patent application Ser. No. 13/933,616 are each specifically incorporated herein by reference in their entireties.

Compositions comprising a 3,5-disubstituted-1,2,4-oxadiazole compound that can be used in the methods provided herein also include, but are not limited to, various aqueous suspension concentrates where the 3,5-disubstituted-1,2,4-oxadiazole compound is provided in the form of a suspended solid particulate. Aqueous suspension concentrates comprising 3,5-disubstituted-1,2,4-oxadiazole compounds in a solid particulate form and methods of making the same disclosed in co-assigned U.S. patent application Ser. No. 13/933,616 are specifically incorporated herein by reference in their entireties.

Compositions comprising a 3,5-disubstituted-1,2,4-oxadiazole compound can improve SCN resistance in soybean germplasm that exhibits at least moderate resistance to at least one race of SCN. Such improvements in SCN resistance can be obtained when the compound treated soybean germplasm is challenged with SCN at about 500 to about 1,000 SCN eggs per 100 cubic centimeters of soil or with about 1,000 to about 2,000 SCN eggs per 100 cubic centimeters of soil. In some embodiments, the improvements in SCN resistance are obtained when the soybean germplasm that exhibits at least moderate resistance to at least one race of SCN is challenged with another SCN race that the soybean germplasm is susceptible to. In some embodiments, the improvements in yield that are obtained by using the 3,5-disubstituted-1,2,4-oxadiazole compound in combination with the SCN resistant soybean germplasm exceed the improvements in yield obtained by use of the soybean germplasm alone or the compound alone. In some embodiments, the reduction in SCN reproduction that is obtained by using the 3,5-disubstituted-1,2,4-oxadiazole compound in combination with the SCN resistant soybean germplasm is the additive sum of improvements in yield obtained by use of the soybean germplasm alone and the compound alone. In some embodiments, the reduction in SCN reproduction that is obtained by using the 3,5-disubstituted-1,2,4-oxadiazole compound in combination with the SCN resistant soybean germplasm is greater than the additive sum of the improvements in yield obtained by use of the soybean germplasm alone and the compound alone. In some embodiments, the improvement in SCN resistance in the SCN germplasm that is obtained by use of the 3,5-disubstituted-1,2,4-oxadiazole compound comprises at least about a 5%, 10%, 20%, 30%, or greater reduction in SCN reproduction in the SCN resistant germplasm treated with the compound in comparison to the SCN resistant germplasm that has not been treated with the compound. In some embodiments, the improvement in SCN resistance in the SCN germplasm that is obtained by use of the 3,5-disubstituted-1,2,4-oxadiazole compound comprises at least about a 5%, 10%, 20%, 30%, or greater reduction in SCN reproduction in the SCN resistant germplasm treated with the compound in comparison to the SCN susceptible germplasm that has been treated with the compound. In some embodiments, an SCN resistant germplasm that is moderately resistant to a first race of SCN yet sensitive to a second race of SCN can exhibit moderate resistance to the second race of SCN when treated with the compound. In one specific embodiment, soybean germplasm that is derived from PI18788 that is susceptible to Race 1 SCN can exhibit moderate resistance to Race 1 SCN when treated with the compound that exceeds the resistance to Race 1 SCN conferred by the germplasm alone or the compound alone.

Compositions comprising a 3,5-disubstituted-1,2,4-oxadiazole compound can also improve yield in soybean germplasm that exhibits at least moderate resistance to at least one race of SCN. Such improvements in yield can be obtained when the compound treated soybean germplasm is challenged with SCN at about 500 to about 1,000 SCN eggs per 100 cubic centimeters of soil or with about 1,000 to about 2,000 SCN eggs per 100 cubic centimeters of soil or with about 2,000 SCN eggs or greater per 100 cubic centimeters of soil. In some embodiments, the improvements in yield are obtained when the soybean germplasm that exhibits at least moderate resistance to at least one race of SCN is challenged with another SCN race that the soybean germplasm is susceptible to. In certain embodiments, the improvements in yield that are obtained by using the 3,5-disubstituted-1,2,4-oxadiazole compound in combination with the SCN resistant soybean germplasm exceed the improvements in yield obtained by use of the soybean germplasm alone or the compound alone. In some embodiments, the improvement in yield that is obtained by using the 3,5-disubstituted-1,2,4-oxadiazole compound in combination with the SCN resistant soybean germplasm is the additive sum of improvements in yield obtained by use of the soybean germplasm alone and the compound alone. In certain embodiments, the improvement in yield that is obtained by using the 3,5-disubstituted-1,2,4-oxadiazole compound in combination with the SCN resistant soybean germplasm is greater than the additive sum of the improvements in yield obtained by use of the soybean germplasm alone and the compound alone. In certain embodiments, the improvement in yield in the SCN germplasm that is obtained by use of the 3,5-disubstituted-1,2,4-oxadiazole compound comprises at least about a 5%, 10%, 20%, 30%, or greater improvement in yield in SCN resistant germplasm treated with the compound in comparison to SCN resistant germplasm that has not been treated with the compound. In some embodiments, the improvement in yield in the SCN germplasm that is obtained by use of the 3,5-disubstituted-1,2,4-oxadiazole compound comprises at least about a 5%, 10%, 20%, 30%, or greater improvement in yield in SCN resistant germplasm treated with the compound in comparison to SCN susceptible germplasm that has been treated with the compound. In some embodiments, an SCN resistant germplasm that is moderately resistant to a first race of SCN yet sensitive to a second race of SCN can exhibit moderate resistance to the second race of SCN when treated with the 3,5-disubstituted-1,2,4-oxadiazole compound. In another embodiment, soybean germplasm that is derived from PI18788 that is susceptible to Race 1 SCN can exhibit moderate resistance to Race 1 SCN when treated with the 3,5-disubstituted-1,2,4-oxadiazole compound that exceeds the resistance to Race 1 SCN conferred by the germplasm alone or the 3,5-disubstituted-1,2,4-oxadiazole compound alone.

In other embodiments, compositions comprising a 3,5-disubstituted-1,2,4-oxadiazole compound and an SCN resistant seed may further comprise additional pesticidal actives including, but not limited to, fungicides and insecticides. In one embodiment, the fungicides and insecticides are selected from the group consisting of strobilurins (e.g. pyraclostrobin, azoxystrobin, and fluoxastrobin), triazoles (e.g. ipconazole and prothioconazole), neonicotinoids (e.g. clothianidin, thiamethoxam, and imidacloprid), phenylamides (e.g. metalaxyl and mefenoxam), diamides (e.g. cyantraniliprole and chlorantraniliprole), carboxamides (e.g. fluxapyroxad, fluopyram, and sedaxane), phenylpyrroles (e.g. fludioxonil), and benzimidazoles (e.g. thiabendazole).

In some embodiments, the present disclosure provides soybean seeds comprising a SCN resistance locus combination conferring low or moderate resistance to one or more races of SCN selected from the group consisting of races 1 to 16, wherein the soybean seeds are coated with a composition comprising a 3,5-disubstituted-1,2,4-oxadiazole compound. In other embodiments, soybean seeds provided herein are coated with a 3,5-disubstituted-1,2,4-oxadiazole compound at a dosage selected from the group consisting of about 0.005, 0.01, 0.05, 0.1, 0.2, 0.3, 0.4, 0.5, 0.6, 0.7, 0.8, 1.0, 1.5, and 2.0 mg/seed.

In some embodiments, the present disclosure further provides methods of growing a soybean plant in a field having medium or high SCN pressure, which methods comprise: (a) planting in a field having medium or high SCN pressure a soybean seed comprising a SCN resistance locus combination conferring low or moderate resistance to one or more races of SCN selected from the group consisting of races 1 to 16, wherein the soybean seed is coated with a composition comprising a 3,5-disubstituted-1,2,4-oxadiazole compound; and (b) growing a soybean plant from the soybean seed. The level of SCN pressure in a field can be evaluated according to the scale in Table 8. The SCN pressure can be selected from the group consisting of between 250 and 500, between 350 and 600, between 450 and 700, between 550 and 800, between 650 and 900, between 750 and 1000, between 850 and 1100, between 950 and 1200, between 1050 and 1300, between 1150 and 1400, between 1250 and 1500, between 1350 and 1600, between 1450 and 1700, between 1550 and 1800, between 1650 and 1900, between 1750 and 2000 SCN eggs per 100 cubic centimeters of soil.

Systems, including automated systems for selecting plants that comprise a marker of interest and/or for correlating presence of the marker with tolerance are also a feature of the disclosure. These systems can include probes relevant to marker locus detection, detectors for detecting labels on the probes, appropriate fluid handling elements and temperature controllers that mix probes and templates and/or amplify templates and systems instructions that correlate label detection to the presence of a particular marker locus or allele.

In an aspect, this invention could be used on any plant selected from the genus *Glycine Willd*. In another aspect, the plant is selected from the species *Glycine max* (domesticated soybean) or *Glycine soja* (wild soybean).

In a preferred aspect, the present disclosure provides a plant to be assayed for resistance or susceptibility to disease by any method to determine whether a plant is resistant, susceptible, or whether it exhibits some degree of resistance or susceptibility. Populations of plants can be similarly characterized in this manner, or further characterized as segregating for the trait of disease tolerance.

It is further understood that a plant of the present disclosure may exhibit the characteristics of any relative maturity group. In an aspect, the maturity group is selected from the group consisting of early maturing varieties, mid-season maturing varieties, and full season varieties.

The present disclosure also provides for parts of the plants of the present disclosure. Plant parts, without limitation, include seed, endosperm, ovule and pollen. In a particularly preferred aspect of the present disclosure, the plant part is a seed.

In another aspect, the soybean seed can be subjected to various treatments. For example, the seeds can be treated to improve germination by priming the seeds or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

In another aspect, the soybean plant can show a comparative resistance compared to a non-resistant control soybean plant. In this aspect, a control soybean plant will preferably be genetically similar except for the disease resistance allele or alleles in question. Such plants can be grown under similar conditions with equivalent or near equivalent exposure to the pathogen.

In a further aspect, this disclosure provides processed products made from the disclosed soybean plants. Such products include, but are not limited to, meal, oil, plant extract, starch, or fermentation or digestion products.

Various patent and non-patent publications are cited herein, the disclosures of each of which are incorporated herein by reference in their entireties.

As various modifications could be made in the constructions and methods herein described and illustrated without departing from the scope of the disclosure, it is intended that all matter contained in the foregoing description or shown in the accompanying drawings shall be interpreted as illustrative rather than limiting. The breadth and scope of the present disclosure should not be limited by any of the above-described exemplary embodiments, but should be defined only in accordance with the following claims appended hereto and their equivalents.

Descriptions of commonly used breeding terms and methods for crossing and producing varieties that are used to describe present disclosure can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), *Center for Agricultural Publishing and Documentation,* 1979; Fehr, In: Soybeans: Improvement, Production and Uses, 2nd Edition, Monograph., 16:249, 1987; Fehr, "Principles of variety development," *Theory and Technique*, (Vol. 1) and *Crop Species Soybean* (Vol. 2), Iowa State Univ., Macmillan Pub. Co., NY, 360-376, 1987).

The definitions and methods provided define the present disclosure and guide those of ordinary skill in the art in the practice of the present disclosure. Unless otherwise noted, terms are to be understood according to conventional usage by those of ordinary skill in the relevant art. Examples of resources describing many of the terms related to molecular biology used herein can be found in in Alberts et al., Molecular Biology of The Cell, $5^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes Icorn, Oxford University Press: New York, 2007. The nomenclature for DNA bases as set forth at 37 CFR § 1.822 is used.

Definitions

Terms defined herein have meanings as commonly understood by a person of ordinary skill in the areas relevant to the present disclosure. Terms such as "a", "an" and "the" are not intended to refer to only a singular entity, but include the general class of which a specific example may be used for illustration. The terminology herein is used to describe specific embodiments of the disclosure, but their usage does not delimit the invention, except as outlined in the claims.

"Allele" generally refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self fertilization (selfing).

"Elite line" means any line that has resulted from breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean. In contrast, an "exotic line" or "exotic germplasm" is a line or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

"Gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Resistance allele" means the nucleic acid sequence associated with resistance or tolerance to disease.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tolerance" or "improved tolerance" in a plant to disease conditions is an indication that the plant is less affected by disease conditions with respect to yield, survivability and/or other relevant agronomic measures, compared to a less tolerant, more "susceptible" plant. Tolerance is a relative term, indicating that a "tolerant" plant survives and/or produces better yields in disease conditions compared to a different (less tolerant) plant (e.g., a different soybean line strain) grown in similar disease conditions. As used in the art, disease "tolerance" is sometimes used interchangeably with disease "resistance." One of skill will appreciate that plant tolerance to disease conditions varies widely, and can represent a spectrum of more-tolerant or less-tolerant phenotypes. However, by simple observation, one of skill can generally determine the relative tolerance or susceptibility of different plants, plant lines or plant families under disease conditions, and furthermore, will also recognize the phenotypic gradations of "tolerant."

EXAMPLES

Reference is now made to the following examples, which together with the above descriptions, illustrate the disclosure in a non-limiting fashion.

Example 1: Inoculation and Assessment of SCN Resistant Phenotypes

Soybean plants are inoculated 1 week after planting by injecting a solution containing 2000 *Heterodera glycines* eggs one inch from the base of the stem. Twenty-eight (28) days after inoculation, the severity of the Soybean Cyst Nematode infestation in each plant is visually assessed by counting the number of cysts extracted from the root ball using a sieve extractor. The number of female cysts on each plant is compared to that of a susceptible check. The average number of female cysts on a standard susceptible check (commonly Lee74) should be ≥100. The Female Index (FI) is calculated by dividing the number of cysts per sample plant by the number of cysts on the susceptible check plant (Schmitt and Shannon, *Crop Science,* 32:275-277(1992)). A rating of disease resistance is assigned based on the thresholds in Table 4.

TABLE 4

Rating Scale of Relative SCN Tolerance Phenotypes

| Female Index (FI) % Lee74 | Rating |
|---|---|
| <10 | R (Resistant) |
| 10 to 22 | MR (Moderately Resistant) |
| >22 to 40 | MS-MR (Moderately Susceptible to Moderately Resistant) |
| >40 | S (Susceptible) |

Example 2: Assays Useful for Detecting rhg1d-Mediated SCN Resistant Genotypes

Peking-derived race 1 resistance to SCN can be obtained by concurrently selecting for rhg1, Rhg4, and rhg1d resistance alleles. Detection of rhg1 and Rhg4 SCN resistance alleles can be achieved using the methods described previously in U.S. Pat. No. 7,485,770 and the academic literature. For convenience, primer sequences for amplifying SNP marker loci linked to the rhg1d resistance allele and the probes used to genotype the corresponding SNP sequences are provided in Table 5. Other primer and probe sequences can be generated and is within the skill of the art, for example using the sequences of Table 3. One of skill in the art will also immediately recognize that other sequences to either side of the given primers can be used in place of the given primers, so long as the primers can amplify a region that is physically linked to the allele to be detected. Further, it will be appreciated that the precise probe to be used for detection can vary, e.g., any probe that can identify the region of a marker amplicon to be detected can be substituted for those examples provided herein. Also, configuration of the amplification primers and detection probes can, of course, vary. Thus, the disclosure is not limited to the primers, probes, or marker sequences specifically recited herein.

Illustrative rhg1d-mediated SCN resistance marker DNA sequences SEQ ID NOs: 25, 26, 27, 28, 30, 33, 38 or 40 can be amplified using the primers indicated in Table 6 using SEQ ID NOs: 45 and 46, 61 and 62, 65 and 66, 69 and 70, 73 and 74, 49 and 50, 53 and 54, or 57 and 58, respectively, and detected with probes indicated in Table 6 as SEQ ID NOs: 47 and 48, 63 and 64, 67 and 68, 71 and 72, 75 and 76, 51 and 52, 55 and 56 or 59 and 60, respectively.

Example 3: Marker-Trait Association Studies

Observing that SCN race 1 resistance does not transmit to progeny plants as expected based on a two gene model, 400 pre-commercial lines are analyzed for patterns of co-segregation of genetic haplotypes with the SCN race 1 resistance phenotype. For comparison, Peking, Forest, PI88788, Williams and Essex lines are included in the analysis. Analysis of the genetic fingerprints and SCN race 1 resistance data from over 400 pre-commercial lines reveal the co-segregation of rhg1, Rhg4, and haplotypes in a 33 cM region on LG B1 with resistant and susceptible phenotypes in Peking-derived lines. Further analysis reveals that the co-segregating region on LG B1 includes a duplication of rhg1. This duplicated locus is named rhg1d. Resistance to SCN race 1, in at least Peking derived lines requires the presence of all three regions: rhg1, Rhg4 and rhg1d. The haplotypes and phenotypes are presented in Table 5.

The results of the marker-trait association study are also confirmed in a phenotypic study of nearly 300 pre-commercial lines derived from a Peking background. A panel of markers is run to select for the presence of both Peking-derived rhg1 and Rhg4 in all lines. Markers are also run to select for the presence and absence of the rhg1d resistance allele. The lines are then screened for race 1 SCN resistance as described in Example 1. The concurrent selection for rhg1, Rhg4, and rhg1d resistance alleles resulted in a 5-fold reduction in the FI compared to concurrent selection for only rhg1 and Rhg4 (FIG. 1). When inoculated with race 3 SCN, the lines containing rhg1, Rhg4, and rhg1d resistance alleles and the lines containing only rhg1 and Rhg4 react with a similar level of resistance (FIG. 2).

TABLE 5

Haplotypes associated with the rhg1d resistance allele and exemplary markers used to predict Peking-derived race 1 SCN resistance

| Line | Rating | SEQ ID NO. 26 | SEQ ID NO. 27 | SEQ ID NO. 28 | SEQ ID NO. 29 | SEQ ID NO. 30 |
|---|---|---|---|---|---|---|
| Peking | R | CC | GG | TT | CC | AA |
| PI88788 | S | CC | TT | AA | CC | AA |
| Williams82 | S | CC | TT | AA | CC | TT |
| Essex | S | TT | TT | AA | CC | TT |

TABLE 6

Primers and probes useful for detecting rhg1d-mediated SCN resistance

| | | | | SEQ ID NO. | | | |
|---|---|---|---|---|---|---|---|
| SEQ ID NO. | SNP pos | Allele 1 | Allele 2 | Fwd Primer | Rev Primer | Probe 1 | Probe 2 |
| 25 | 201 | T | G | 45 | 46 | 47 | 48 |
| 26 | 201 | T | C | 61 | 62 | 63 | 64 |
| 27 | 201 | T | G | 65 | 66 | 67 | 68 |
| 28 | 81 | A | T | 69 | 70 | 71 | 72 |
| 30 | 201 | A | T | 73 | 74 | 75 | 76 |
| 33 | 532 | G | A | 49 | 50 | 51 | 52 |
| 38 | 564 | C | T | 53 | 54 | 55 | 56 |
| 40 | 201 | A | T | 57 | 58 | 59 | 60 |

The co-segregation of genetic haplotypes and SCN phenotypes is further confirmed in a study of historic data from 900 pre-commercial lines spanning 4 growing season. These lines are included in an association study to map SCN resistance factors. The marker-trait association study confirmed the importance of rhg1d on LG B1 along with the known SCN resistance loci rhg1 and Rhg4 on LGs G and A2, respectively (Table 7).

TABLE 7

Race 1 SCN resistance loci identified from historic data

| LG | Resistance locus | Pos (peak) | cM Interval | −Log10(P) | % var |
|---|---|---|---|---|---|
| G | rhg1 | 13.7 | 12.5-20.9 | 8.7 | 0.24 |
| A2 | Rhg4 | 66.7 | 63.0-68.2 | 5.6 | 0.00 |
| B1 | rhg1d | 160.3 | 144.0-177.6 | 12.0 | 0.29 |

Example 4:
3-Phenyl-5-(thiophen-2-yl)-1,2,4-oxadiazole Provides Enhanced Control of SCN in a Transgenic Race 2 Resistant Line in Greenhouse Studies Various soybean lines were treated with the compound 3-phenyl-5-(thiophen-2-yl)-1,2,4-oxadiazole following standard industry protocols. The structure of 3-phenyl-5-(thiophen-2-yl)-1,2,4-oxadiazole is:

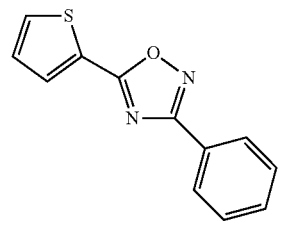 [SMILES: c1ccc(-c2noc(-c3cccs3)n2)cc1]

Untreated seed or seed treated only with a colorant were used as standard controls. Single soybean seed were planted in 3"×3" pots filled with field soil mixed with sand and steam sterilized. Ten days after germination seedlings were inoculated with 2000-3000 SCN eggs isolated from cultures maintained on the appropriate soybean germplasm to maintain designated race. After inoculation, soil temperatures were maintained at 28° C. with 16-hour day-length for 28-30 days. On the last day of the incubation period, individual plants were uprooted. Cysts from each plant were collected by blasting the roots with pressurized water and washing the soil while trapping the released cysts on sieves. The collected cysts from individual plants were transferred to a counting dish. The total number of cysts from individual plants was counted under a dissecting microscope. Data is reported as the number of cysts collected from an individual pot and represent the mean of 6-8 replications.

Figure 3:
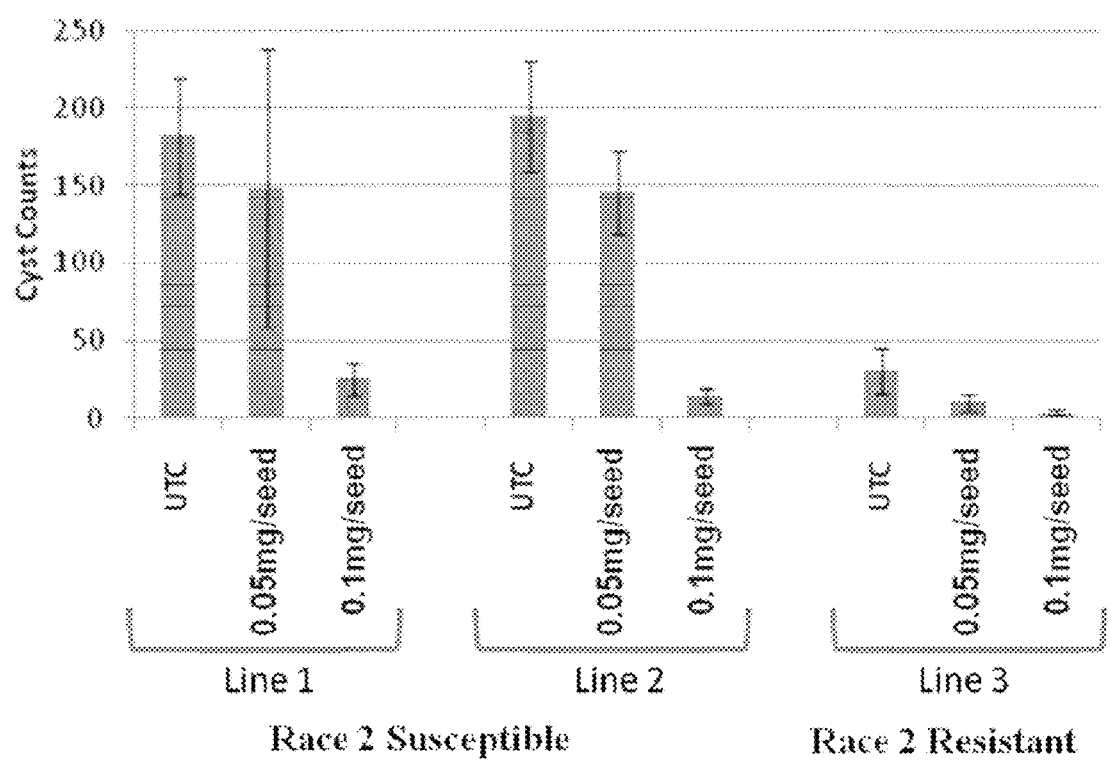
FIG. 3 shows the number of SCN cysts on soybean roots in greenhouse studies of seeds treated with 3-phenyl-5-(thiophen-2-yl)-1,2,4-oxadiazole where two SCN race 2 susceptible soybean lines and an SCN resistant soybean line were challenged with race 2 SCN according to an aspect of the present disclosure.
Figure 4:
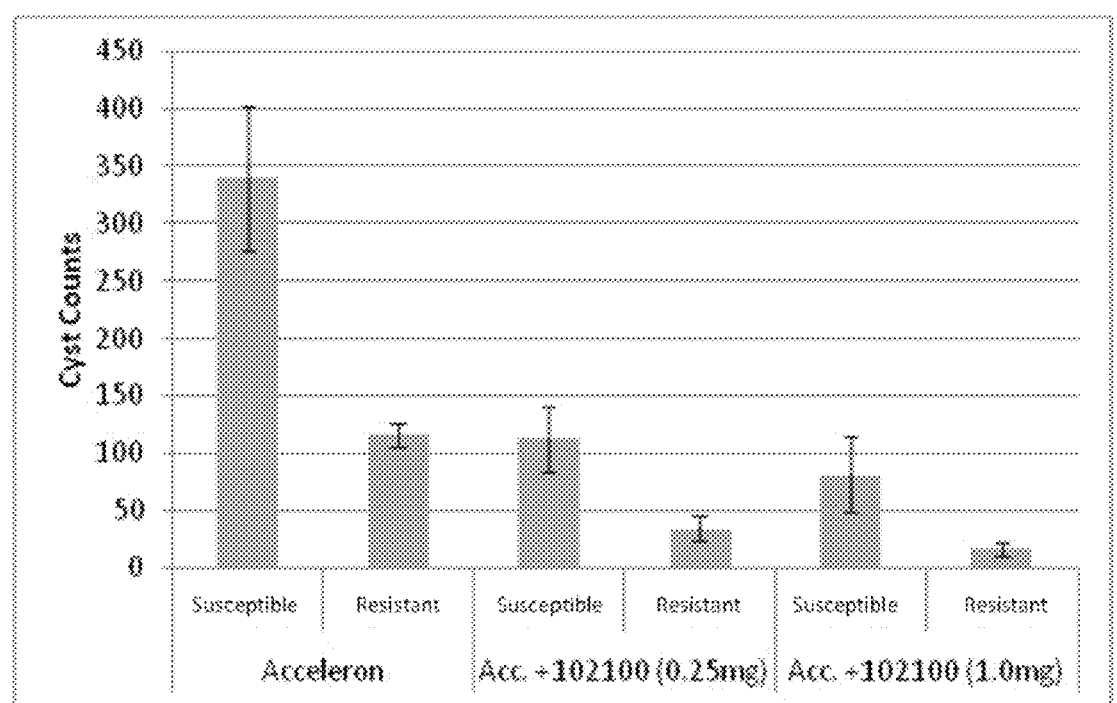
FIG. 4 shows the number of SCN cysts on soybean roots in greenhouse studies of seeds treated with Acceleron® alone or in combination with 3-phenyl-5-(thiophen-2-yl)-1,2,4-oxadiazole where a SCN susceptible soybean line and an SCN resistant soybean line were challenged with SCN according to an aspect of the present disclosure.

The results of the green house evaluations provided in FIG. 3 show that treatment with 3-phenyl-5-(thiophen-2-yl)-1,2,4-oxadiazole enhances resistance to race 2 SCN. Trials where a susceptible soybean line were challenged with SCN in the presence and absence of 3-phenyl-5-(thiophen-2-yl)-1,2,4-oxadiazole also show that the 3-phenyl-5-(thiophen-2-yl)-1,2,4-oxadiazole treatment provided lower SCN cyst counts. All plants were treated with ACCELERON® (Monsanto Company, St. Louis, Mo., USA) to reduce fungal disease.

Example 5: Improved Control of SCN in Field Tests

Prior to planting, seeds were treated with chemistry according to standard industry protocols. Six different untreated and treated lines were planted in eight plots. The six lines were selected based on resistance reaction to race 1 and race 3 SCN. Three lines were from Peking source germplasm and displayed either sensitivity, moderate resistance or resistance to SCN. Three lines were from PI88788 source germplasm and displayed either sensitivity, moderate resistance or resistance to SCN. The levels of resistance were determined essentially as described by Schmitt, D. P. and Shannon, G., *Crop Sci.*, 32:275-277 (1992), according to Table 4.

Soil cores were collected at emergence near the root zone of the plant. Multiple soil samples were taken, combined, and crushed into small evenly-sized particles. A sample aliquot was combined with water allowed to sit, then stirred. The sample was then poured into a funnel and processed in a soil elutriator. The sample was counted, with a final number being given as eggs per 100 cc of soil. Based on the number of eggs per 100 cc of soil, the field was classified as low to high pressure, where about 0 to about 180 eggs per 100 cc of soil was considered to be low pressure, about 180 eggs to about 1100 eggs per 100 cc of soil was considered to be medium pressure, and greater than about 1100 eggs per 100 cc of soil was considered to be high pressure. The scale for evaluating SCN Pressure is provided in Table 8.

TABLE 8

SCN Field Pressure Scale

| SCN Pressure | Eggs/100 cc Soil | Potential Yield Loss of Susceptible Variety |
| --- | --- | --- |
| Low | 0 | 0% |
| Low | 1-182 | 0% to 5% |
| Med | 183-363 | 5% to 15% |
| Med | 364-1090 | 15% to 20% |
| High | Above 1100 | >20% high |

Figure 5:
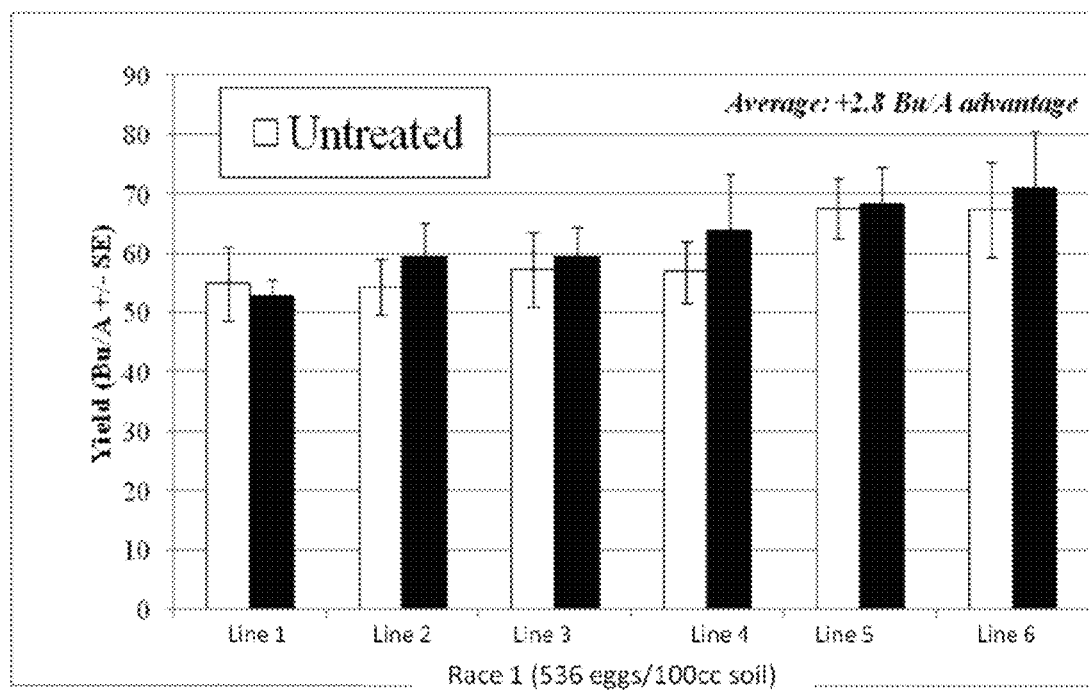
FIG. 5 shows an increase in yield obtained in field tests under low race 1 SCN pressure (i.e., about 536 SCN eggs/100 cc soil) using 3-phenyl-5-(thiophen-2-yl)-1,2,4-oxadiazole according to an aspect of the present disclosure.
Figure 6:
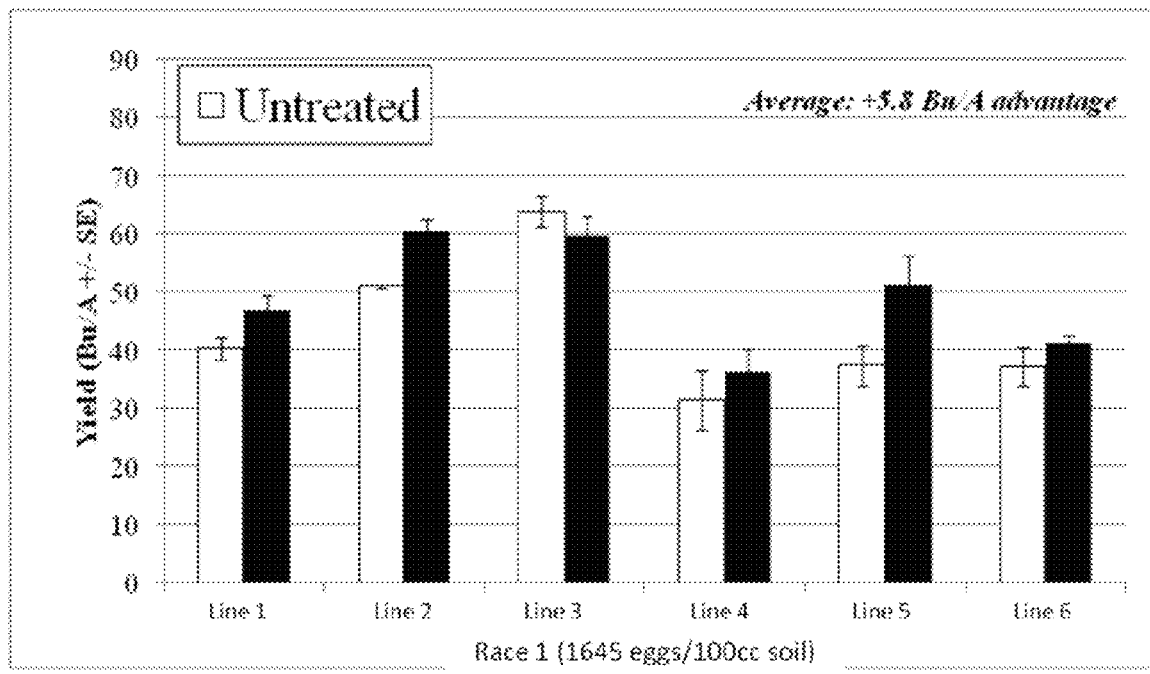
FIG. 6 shows an increase in yield obtained in field tests, under high race 1 SCN pressure (i.e., about 1645 SCN eggs/100 cc soil) using 3-phenyl-5-(thiophen-2-yl)-1,2,4-oxadiazole according to an aspect of the present disclosure.

Lines were planted in four medium and four high pressure fields containing race 1 soybean cyst nematodes. The medium pressure fields contained 536 eggs per 100 cc of soil while the high pressure fields contained 1645 eggs per 100 cc of soil. Yield was determined at harvest. The lines derived from Peking germplasm provided protection against race 1 SCN while the lines derived from PI88788 germplasm provided protection against race 3 SCN. No statistical difference in yield between 3-phenyl-5-(thiophen-2-yl)-1,2,4-oxadiazole untreated and treated groups of Peking or PI88788-sensitive, -moderately resistant and -resistant lines was observed in the medium pressure field (FIG. 5). In the high pressure field, a Peking-sensitive line (Line 1) treated with 3-phenyl-5-(thiophen-2-yl)-1,2,4-oxadiazole had a statistically higher yield than untreated. Peking-resistant (Line 3), PI88788-sensitive (Line 4) and PI88788-resistant (Line 6) lines showed no statistical difference between 3-phenyl-5-(thiophen-2-yl)-1,2,4-oxadiazole treated and untreated in the high pressure field. Peking-moderately resistant (Line 2) and PI88788-moderately resistant (Line 5) treated with 3-phenyl-5-(thiophen-2-yl)-1,2,4-oxadiazole had a unexpected statistically higher yield than untreated Peking-moderately resistant (Line 2) and PI88788-moderately resistant (Line 5) in the high SCN race 1 pressure field (FIG. 6). A description of the lines is provided in Table 9. The two moderately resistant lines with treatment demonstrate on average a 5.8 bushel per acre advantage compared to untreated in the high pressure field.

TABLE 9

Soybean lines used in field tests

| Name | Source | SCN Rating |
| --- | --- | --- |
| Line 1 | Peking | R |
| Line 2 | Peking | MR |
| Line 3 | Peking | S |
| Line 4 | PI88788 | R |
| Line 5 | PI88788 | MR |
| Line 6 | PI88788 | S |

Example 6: Increased Yield in Field Tests

Eleven different untreated and treated lines were planted in a total of 43 separate field trials with a single variety per location. The eleven lines were selected based on their resistance reactions to race 3 SCN. The eleven lines were developed from PI88788 source germplasm and display either moderate resistance or resistance to race 3 SCN.

3-Phenyl-5-(thiophen-2-yl)-1,2,4-oxadiazole was combined with commercial fungicides and insecticides in a tank slurry mix with colorant, polymer, and water at the recommended rates and allowed to mix thoroughly. Using a Gustafson continuous batch seed coater the seed batch was loaded, the treatment slurry was injected and the mixture was allowed to tumble for 35-40 seconds before being ejected into a paper storage bag.

Predictive nematode sampling was conducted prior to field trial implementation to ensure appropriate levels of nematode pressure. In the trial areas used, the nematode pressure was moderate to high (see Table 8). Trial areas were divided into 2 acre sections based upon soil type, crop history, tillage, drainage, fertilization and other agronomic factors. Within each field section, 10 to15 soil cores were collected to a total depth of 6 to 8 inches using a zigzag pattern. The soil cores for each treatment area were placed in a bucket and gently mixed thoroughly without crushing to create a composite soil sample for each plot. Sub-samples (~1 pint of soil) were taken from each composite sample and placed in a plastic bag, with appropriate handling to ensure viability of nematodes, and sent to a lab for nematode quantification.

The experimental design for field trials consisted of strip plots (8 rows×250 ft) wherein each strip represents one replication. Seeds, treated as described above, were planted at densities representative of standard agronomic practice. Foliar herbicides, fungicides and/or insecticides were applied as needed per standard agronomic practice.

Quantitative in-season nematode sampling using root and soil samples was conducted eight weeks after planting for trials. For root sampling, using a zigzag pattern, 5 living plants from each treatment were extracted from the soil, ensuring the roots remained intact and enclosed with enough soil to keep the roots from drying out. The tops of the plants were cut off at the soil line and the soil coated roots were placed in a plastic bag. Soil sampling was conducted as described above for the predictive nematode sampling. Samples were sent to a lab for nematode quantification.

Yield data was collected using commercially available harvesting equipment to harvest each plot. The data were calculated to represent bushels per acre by taking the grain weight over the square footage of each plot and adjusting to 13% moisture.

TABLE 10

Average Yield Data

| Treatment | Fungicide/ Insecticide | Nematicide | Yield (BU/A) |
| --- | --- | --- | --- |
| Commercial Standard | Fungicide + Insecticide (Base 1) | Commercial Nematicide 1 | 53.7 |
| Commercial Standard | Fungicide + Insecticide (Base 2) | 3-phenyl-5-(thiophen-2-yl)- 1,2,4-oxadiazole (0.50 mg AI/seed) | 55.7 |

The invention claimed is:

1. A method for creating a population of soybean plants with enhanced race 1 soybean cyst nematode (SCN) resistance, said method comprising:
   (a) crossing a first soybean plant with a second soybean plant to provide a first population of soybean plants;
   (b) concurrently genotyping said first population of soybean plants for the presence of:
      (i) a first genetic marker that is genetically linked to an rhg1 resistance allele by 10 centimorgans (cM) or less;
      (ii) a second genetic marker that is genetically linked to an Rhg4 resistant allele by 10 cM or less; and
      (iii) a third genetic marker that is genetically linked to an rhg1d resistance allele on linkage group B1 by 10 cM or less selected from the group consisting of:
         SEQ ID NO: 25, comprising a T or G at position 201;
         SEQ ID NO: 26, comprising a T or C at position 201;
         SEQ ID NO: 27, comprising a T or G at position 201;
         SEQ ID NO: 28, comprising an A or T at position 81;
         SEQ ID NO: 30, comprising an A or T at position 201;
         SEQ ID NO: 33, comprising a G or A at position 532;
         SEQ ID NO: 38, comprising a C or T at position 564; and
         SEQ ID NO: 40, comprising an A or T at position 201; and
   (c) selecting one or more soybean plants or seeds comprising said first genetic marker, said second genetic marker, and said third genetic marker from said first population of soybean plants, wherein said one or more soybean plants or seeds comprise enhanced race 1 SCN resistance.

2. The method of claim 1, wherein said first genetic marker is genetically linked to rhg1 by less than 8 cM.

3. The method of claim 2, wherein said first genetic marker is genetically linked to rhg1 by less than 7.5 cM.

4. The method of claim 3, wherein said first genetic marker is genetically linked to rhg1 by less than 5 cM.

5. The method of claim 4, wherein said first genetic marker is genetically linked to rhg1 by less than 1 cM.

6. The method of claim 5, wherein said first genetic marker is genetically linked to rhg1 by less than 0.5 cM.

7. The method of claim 1, wherein said second genetic marker is genetically linked to Rhg4 by less than 8 cM.

8. The method of claim 7, wherein said second genetic marker is genetically linked to Rhg4 by less than 7.5 cM.

9. The method of claim 8, wherein said second genetic marker is genetically linked to Rhg4 by less than 5 cM.

10. The method of claim 9, wherein said second genetic marker is genetically linked to Rhg4 by less than 1 cM.

11. The method of claim 10, wherein said second genetic marker is genetically linked to Rhg4 by less than 0.5 cM.

12. The method of claim 1, wherein said soybean cyst nematode is *Heterodera glycines*.

13. The method of claim 1, wherein said genetic markers are selected from the group consisting of a randomly amplified polymorphic DNA (RAPD) marker, a restriction fragment length polymorphism (RFLP) marker, a single nucleotide polymorphism (SNP) marker, an amplified fragment length polymorphism (AFLP) marker, and a simple sequence repeat (SSR) marker.

14. The method of claim 1, wherein said method further comprises:
(d) producing a second population of progeny from at least one of said selected soybean plants selected in step (c) via
(i) self-pollinating said selected soybean plants; or
(ii) crossing said one or more selected soybean plants with a second soybean plant,
wherein at least one soybean plant of said second population comprises said at least one of said genetic markers genotyped in step (b) and said rhg1d resistance allele.

15. The method of claim 1, wherein said third genetic marker is genetically linked to rhg1d by less than 8 cM.

16. The method of claim 15, wherein said third genetic marker is genetically linked to rhg1d by less than 7.5 cM.

17. The method of claim 16, wherein said third genetic marker is genetically linked to rhg1d by less than 5 cM.

18. The method of claim 17, wherein said third genetic marker is genetically linked to rhg1d by less than 1 cM.

19. The method of claim 18, wherein said third genetic marker is genetically linked to rhg1d by less than 0.5 cM.

20. The method of claim 1, wherein said third genetic marker is located between SEQ ID NOs: 1 and 44.

21. The method of claim 1, wherein said rhg1d allele is obtainable from Line 1 (Peking).

* * * * *